US011136614B2

(12) United States Patent
Messner et al.

(10) Patent No.: US 11,136,614 B2
(45) Date of Patent: Oct. 5, 2021

(54) LIVE-CELL SEEDING METHOD FOR MICROARRAYS

(71) Applicant: ARIZONA BOARD OF REGENTS ON BEHALF OF ARIZONA STATE UNIVERSITY, Scottsdale, AZ (US)

(72) Inventors: Jacob Messner, Mesa, AZ (US); Clifford Anderson, Tempe, AZ (US); Honor Glenn, Mesa, AZ (US); Kristen Lee, Mesa, AZ (US); Mark Richards, Chandler, AZ (US); Laimonas Kelbauskas, Gilbert, AZ (US); Kimberly Bussey, Phoenix, AZ (US); Deirdre Meldrum, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 204 days.

(21) Appl. No.: 15/757,712

(22) PCT Filed: Oct. 7, 2016

(86) PCT No.: PCT/US2016/056058
§ 371 (c)(1),
(2) Date: Mar. 6, 2018

(87) PCT Pub. No.: WO2017/062807
PCT Pub. Date: Apr. 13, 2017

(65) Prior Publication Data
US 2018/0334700 A1  Nov. 22, 2018

Related U.S. Application Data

(60) Provisional application No. 62/238,298, filed on Oct. 7, 2015.

(51) Int. Cl.
*C12Q 1/24* (2006.01)
*C12M 1/00* (2006.01)
*C12M 1/32* (2006.01)
*G01N 33/569* (2006.01)

(52) U.S. Cl.
CPC ............... *C12Q 1/24* (2013.01); *C12M 1/00* (2013.01); *C12M 23/12* (2013.01); *G01N 33/56966* (2013.01)

(58) Field of Classification Search
CPC ........... C12Q 1/24; C12M 1/00; C12M 23/12; G01N 33/56966
See application file for complete search history.

(56) References Cited

U.S. PATENT DOCUMENTS

| 2003/0025008 | A1* | 2/2003 | Srinivasan | A61M 15/0028 239/589 |
| 2005/0106607 | A1* | 5/2005 | Yin | B01L 3/5085 435/6.11 |
| 2006/0270032 | A1 | 11/2006 | Bhatia et al. | |
| 2008/0131615 | A1* | 6/2008 | Robertson | B05B 5/0255 427/483 |
| 2008/0160539 | A1 | 7/2008 | Murphy et al. | |
| 2008/0220169 | A1 | 9/2008 | Khademhosseini et al. | |
| 2008/0220516 | A1 | 9/2008 | Eddington et al. | |
| 2009/0054264 | A1* | 2/2009 | Ugolin | B01L 3/502707 506/13 |
| 2010/0068793 | A1* | 3/2010 | Ungrin | C12N 5/0606 435/283.1 |
| 2011/0195496 | A1* | 8/2011 | Muraguchi | B01J 19/0046 435/325 |
| 2013/0196435 | A1 | 8/2013 | Lee et al. | |
| 2014/0220555 | A1* | 8/2014 | Chen | C12N 5/0062 435/5 |

FOREIGN PATENT DOCUMENTS

| WO | 2010101708 A2 | 9/2010 |
| WO | 2011094572 A2 | 8/2011 |
| WO | 2011103143 A1 | 8/2011 |

OTHER PUBLICATIONS

Selimovic, S et al. Microfabricated polyester conical microwells for cell culture applications. Lab on a Chip. 2011. 11: 2325-2332. (Year: 2011).*
Anis, Y. H., et al., "Automated Selection and Placement of Single Cells Using Vision-Based Feedback Control," IEEE Transactions on Automation Science and Engineering, vol. 7, Issue 3, Jan. 8, 2010, pp. 598-606.
Dai, W., et al., "Convenient, Reliable, Bias-Free Dynamic Patterning of Multiple Types of Cells into Precisely Defined Micropatterns for Co-Culture Study," ChemNanoMat, vol. 2, Issue 5, Feb. 17, 2016, pp. 447-453.
Etzkorn, J. R., et al., "Using micro-patterned sensors and cell self-assembly for measuring the oxygen consumption rate of single cells," Journal of Micromechanics and Microengineering, vol. 20, Issue 9, Article 095017, Sep. 2010, 11 pages.
Flaim, CJ, et al., "An extracellular matrix microarray for probing cellular differentiation," Nature Methods, vol. 2, Jan. 21, 2005, pp. 119-125.
Folch, A., et al., "Microfabricated elastomeric stencils for micropatterning cell cultures," Journal of Biomedical Materials Research: Part B, Applied Materials, vol. 52, Issue 2, Nov. 2000, pp. 346-353.

(Continued)

*Primary Examiner* — David W Berke-Schlessel
*Assistant Examiner* — Susan E. Fernandez
(74) *Attorney, Agent, or Firm* — Withrow & Terranova, P.L.L.C.; Vincent K. Gustafson

(57) ABSTRACT

Methods for seeding live cells onto spatially defined regions of a substrate including multiple features (e.g., microwells or other microenvironments) utilize a stencil embodied in a hole-defining sacrificial film. A sacrificial film devoid of holes may be applied over features of a substrate, and a hole generating mechanism (e.g., hot needle or laser) aligned with features may be used to define holes in the film. Alternatively, holes may be predefined in a sacrificial film to form a stencil, and the stencil may be assembled to the substrate with the holes registered with features thereof. Thereafter, cells are seeded through holes in the film. Seeded cells are subject to incubation, further processing, and/or performance of one or more assays, and the hole-defining sacrificial film (stencil) may be removed.

8 Claims, 14 Drawing Sheets

(56) References Cited

OTHER PUBLICATIONS

Huang, Z., et al., ""Crk-associated substrate (Cas) signaling protein functions with integrins to specify axon guidance during development,"" Development, vol. 134, Issue 12, Jun. 2007, pp. 2337-2347.
Hughes, M. A., et al., "Modulating patterned adhesion and repulsion of HEK 293 cells on microengineered parylene-C/SiO2 substrates," Journal of Biomedical Materials Research Part A, vol. 101, Issue 2, Feb. 2013, pp. 349-357.
Javaherian, S., et al., "A fast and accessible methodology for micro-patterning cells on standard culture substrates using Parafilm™ inserts," PLoS One, vol. 6, Issue 6, e20909, Jun. 7, 2011, pp. 1-8.
Jung, C.-H., et al., "Patterning of cells on a PVC film surface functionalized by ion irradiation," Polymers Advanced Technologies, vol. 21, Apr. 12, 2009, pp. 135-138.
Lew, C. Y., et al., "Injection moulding of polymer-carbon nanotube composites," Polymer-Carbon Nanotube Composites: Preparation, Properties and Applications, Woodhead Publishing Series in Composites Science and Engineering, 2011, pp. 155-192.
Lew, C. Y., et al., "Preparation and properties of polyolefin-cla nanocomposites," Polymer Engineering and Science, vol. 44, Issue 6, Jun. 2004, pp. 1027-1035.
Li, W., et al., "NeuroArray: A Universal Interface for Patterning and Interrogating Neural Circuitry with Single Cell Resolution," Scientific Reports, vol. 4, Apr. 24, 2014, Article 4784, 7 pages.
Lu, Z., et al., "Single Cell Deposition and Patterning with a Robotic System," PLoS One, vol. 5, Issue 10, Article e13542, Oct. 21, 2010, 9 pages.
Messner, J. J., et al., "Laser-fabricated cell patterning stencil for single cell analysis," BMC Biotechnology, vol. 17, Issue 89, Dec. 19, 2017, pp. 1-9.
Nilsson, J., et al., "Review of cell and particle trapping in microfluidic systems," Analytica Chimica Acta, vol. 649, Jul. 14, 2009, pp. 141-157.
Peterbauer, T., et al., "Simple and versatile methods for the fabrication of arrays of live mammalian cells," Lab on a Chip, vol. 6, Issue 7, Jul. 2006, pp. 857-863.
Rettig, Jr, et al., "Large-scale single-cell trapping and imaging using microwell arrays," Analytical Chemistry, vol. 77, Issue 17, Jul. 30, 2005, pp. 5628-5634.
Tan, S. J. T., et al., "Microdevice for the isolation and enumeration of cancer cells from blood," Biomedical Microdevices, vol. 11, Apr. 23, 2009, pp. 883-892.
Van Tienhoven, E. A. E., et al., "In vitro and in vivo (cyto)toxicity assays using PVC and LDPE as model materials," Journal of Biomedical Materials Research, vol. 78A, Issue 1, Jul. 2006, pp. 175-182.
Wu, J., et al., "Patterning cell using Si-stencil for high-throughput assay," RSC Advances, vol. 1, Issue 5, Aug. 31, 2011, pp. 746-750.
International Search Report and Written Opinion for International Patent Application No. PCT/US2016/056058, dated Dec. 30, 2016, 6 pages.
International Preliminary Report on Patentability for International Patent Application No. PCT/US2016/056058, dated Apr. 10, 2018, 5 pages.
Extended European Search Report for European Patent Application No. 16854/118.4, dataed Apr. 16, 2019, 8 pages.

\* cited by examiner

LIVE-CELL SEEDING METHOD FOR MICROARRAYS

STATEMENT OF RELATED APPLICATION(S)

This application is a 35 U.S.C. § 371 national phase filing of International Application No. PCT/US2016/056058 filed Oct. 7, 2016, and claims the benefit of U.S. Provisional Patent Application No. 62/238,298 filed Oct. 7, 2015, wherein the disclosures of the foregoing applications are hereby incorporated by reference herein in their entireties.

GOVERNMENT RIGHTS IN INVENTION

This invention was made with government support under U01 CA164250 awarded by the National Institutes of Health. The government has certain rights in the invention.

TECHNICAL FIELD

This disclosure relates to spatial positioning and isolation of mammalian cells, including placement of live cells in or on spatially defined regions of a substrate (e.g., microarray substrates including but not limited to microwells), such as may be useful to permit cells to be incubated, processed, and/or analyzed in an array format.

BACKGROUND

The ability to manipulate and selectively localize cells (e.g., mammalian cells) into patterns or distinct microenvironments plays a fundamental role in single cell analysis, tissue engineering, cell signaling studies, drug screening, and cell migration assays. Traditionally, biochemical analysis of cells has been conducted on bulk cell populations producing results that are averaged across thousands or millions of cells. This approach obscures non-normal distribution profiles of the population as well as potentially important contributions from small subpopulations of cells. Recent recognition of the fact that even genetically identical cells can be heterogeneous in physiology, cell fate decisions, and response to stimuli has sparked interest in single cell analysis techniques.

One common approach for a variety of single cell analyses is to physically isolate individual cells so that they can be analyzed independently. Large microwell arrays embody a popular format that allows single cells to be analyzed with sufficient throughput to yield statistically significant information about the cell type under study. There is abundant literature on cell seeding methods for microarrays. Cells can be robotically manipulated one by one into microwells utilizing a vision-assisted "pick and place" approach. Although this approach results in very high efficiency (~90% single cells in microwells), it is low throughput and requires specialized instrumentation and training.

Due to its speed and simplicity, the most widely used method is random seeding, in which a cell suspension is applied to the entire array. With this approach, cells adhere to all surface regions of a substrate with equivalent likelihood. A drawback of this approach is that cells adhere to the lips of the microwells, as well as in the regions outside the microwells, and such adhesion may compromise or interfere with downstream analysis. Another drawback to random seeding directly onto a microwell substrate is that, for microwells having a diameter of more than about 2 or 3 times that of a cell (in a spherical form, prior to attachment and spreading), the distribution of the number of cells per microwell approaches that of a Poisson distribution, which has a theoretical limit of 37% single cell occupancy. For metabolic flux assays, the diameter of the microwell needs to be large enough to prevent the metabolite from being depleted faster than data can be collected.

Another approach to directing preferential cell adhesion, either in microwells or on other surfaces, is to functionalize a surface by patterning extra-cellular matrix proteins or other adhesion-promoting chemistry. A major drawback of preferential adherence methods is the introduction of phenotypically discriminatory selection processes associated with surface treatment. For example, cells in the population that adhere less avidly or less quickly are preferentially lost during rinsing steps. In addition, most cells activate various intracellular signaling pathways in response to adhesion proteins and other chemical treatments may affect cellular physiology in unpredictable ways.

Pre-fabricated masks defining voids have been employed to seed cells selectively on featureless surfaces. See, e.g., S. J. Tan, et al., *Biomed Microdevices*, 2009, 11 883; A. Folch, et al., *J Biomed Mater Res.* 2000, 52, 346; S. Javaherian, et al., *PLos One*, 2011, 6, e20909; W. Li, et al., *Sci. Rep.*, 2014, 4, 4784; J. Wu, et al., *RSC Adv.*, 2011, 1, 746-750; W. Dai, et al., *ChemNanoMat*, 2016; J. R. Etzkorn et al., *J. Micromechanics Microengineering*, 2010, 20, 095017. These provide the simplicity of random seeding with the advantage of restricting cell adhesion to particular locations. However, to adapt this approach in order to restrict cells to specific features of an underlying substrate at predefined locations, such as microwells, the mask would somehow need to be precisely aligned and affixed to the substrate. For a large and densely packed microwell array and a mask with a corresponding array of microscopic holes, this alignment poses a significant challenge.

Inkjet-based cell 'printing' and deposition methods have been proven to be effective at sorting and patterning cells (both in bulk and at a single cell level), but are typically low throughput which limits their utility, and such methods raise concern about cell stress responses.

Other methods for spatial positioning and isolation of cells tend to subject cells to high stress environments, discriminate against certain phenotypes, or are challenging to implement. Many active cell patterning and isolation methods are based on microfluidic systems, whereby cells are manipulated and transported using fluidic forces. Various microfluidic geometries have been used to rapidly pattern cells into hydrodynamic traps, but trap-based approaches tend to discriminate against particular cell morphologies or sizes with pathological relevance for human disease, and also impose difficulties in isolating single cells in distinct microenvironments. Droplet-based microfluidics which encapsulate single cells within medium-oil emulsion droplets are highly effective at rapidly isolating cells, but are poorly suited for studying temporal processes in live cells due to the droplet environment. Various microfluidic patterning and isolation approaches also expose cells to shear stress than may affect cell health, function, and population representation.

The art continues to seek improved methods for selectively localizing cells into patterns or distinct microenvironments and which are capable of overcoming challenges associated with conventional cell localization methods.

SUMMARY

Aspects of this disclosure relate to methods for seeding live cells onto spatially defined regions of a substrate, such as microwells or other desired microenvironments. The method employs a stencil which may be embodied in a biocompatible polymeric film, to improve cell seeding. In certain embodiments, a stencil film devoid of holes is assembled to a microwell array and holes are generated by aligning a hole-generating mechanism or apparatus to the microwells. Alternatively, holes may be generated in the stencil first, and then the stencil with a pattern of holes may be aligned to the microwells. Cells are seeded through holes defined in the stencil and subjected to incubation. The stencil is then subject to removal and/or the cell-containing microarray is subjected to standard array processing thereafter. The disclosed method is robust, simple, high-throughput, and well-suited for achieving high single-cell occupancy rates with minimal presence of cells on microarray lips, and with minimal presence of cells in interstitial areas between cells. Minimization of cells on microarray lips avoids crushing of cells, while minimization of cells in interstitial areas between cells renders a microarray device suitable for metabolic assays that collect oxygen concentration data for assessing leakage rate.

In one aspect, the disclosure relates to a method for seeding cells. The method includes: affixing a sacrificial film to a cell seeding substrate defining a plurality of features (e.g., microwells), wherein each feature of the plurality of features is elevated or recessed relative to a body structure connecting the plurality of features. The method further includes generating an array of holes in the sacrificial film, wherein each hole of the array of holes is registered with a feature of the plurality of features. In certain embodiments, the plurality of features comprises a plurality of microwells. In certain embodiments, the method further includes seeding cells through the array of holes onto the cell seeding substrate to yield a plurality of spatially localized cells.

In certain embodiments, said generating of an array of holes comprises use of a hot needle and/or laser ablation.

In certain embodiments, the array of holes may be generated after the sacrificial film is assembled to the microwell array. In certain embodiments, the method includes incubating the plurality of spatially localized cells seeded onto the cell seeding substrate. Following seeding, cells may be subject to incubation, further processing, and/or performance of one or more assays. In certain embodiments, the method further includes removing the sacrificial film. In certain embodiments, the sacrificial film may be removed at any convenient time before or after any of the foregoing steps.

In certain embodiments, the method further includes performing an assay utilizing the plurality of spatially localized cells, wherein the sacrificial film is removed prior to collection of data from the assay. In certain embodiments, the assay involves measurement of metabolic flux.

In certain embodiments, the sacrificial film comprises a metal. In certain embodiments, the sacrificial film comprises a polymeric film.

In certain embodiments, the method further includes selectively melting portions of the polymeric film onto a cover in multiple locations to locally compromise a structural integrity of the polymeric film and to locally adhere portions of the polymeric film to the cover in the multiple locations. In certain embodiments, the method further includes removal of the cover, whereby upon removal of the cover, the locally adhered portions of the polymeric film remain adhered to the cover.

In certain embodiments, the plurality of features comprises a plurality of microwells; the polymeric film comprises a main film structure, and portions of the polymeric film are deposited into microwells of the plurality of microwells, and said portions are simultaneously separated from the main film structure, such that upon removal of the main film structure, film residue remains in the microwells or is otherwise vaporized or redistributed.

In another aspect, the disclosure relates to a method for seeding cells utilizing a cell seeding substrate defining a plurality of features, wherein each feature of the plurality of features is elevated or recessed relative to a body structure connecting the plurality of features. The method includes: perforating a sacrificial film (e.g., a polymeric film) with a plurality of microholes; aligning the plurality of microholes of the perforated sacrificial film with the plurality of features (e.g., microwells) defined by the cell seeding substrate; and assembling the perforated sacrificial film to the cell seeding substrate.

In certain embodiments, the plurality of features comprises a plurality of microwells. In certain embodiments, the method further includes seeding cells through the plurality of microholes onto the cell seeding substrate to yield a plurality of spatially localized cells. In certain embodiments, the method further includes incubating the plurality of spatially localized cells seeded onto the cell seeding substrate. In certain embodiments, the method further includes removal of the sacrificial film.

In certain embodiments, the method further includes performing an assay utilizing the plurality of spatially localized cells while arranged in or on the cell seeding substrate. The sacrificial film may be removed prior to collection of data from the assay. In certain embodiments, the assay involves measurement of metabolic flux.

In certain embodiments, the sacrificial film comprises a metal. In certain embodiments, the sacrificial film comprises a polymeric film.

In certain embodiments, the polymeric film is selectively melted onto a cover in multiple locations to locally compromise a structural integrity of the polymeric film and to locally adhere portions of the polymeric film to the cover in the multiple locations. In certain embodiments, the method further includes removing the cover, whereby upon removal of the cover, the locally adhered portions of the polymeric film remain adhered to the cover.

In further aspects, any two or more features or aspects of the disclosure may be combined for additional advantage.

BRIEF DESCRIPTION OF THE DRAWINGS

The accompanying drawing figures incorporated in and forming a part of this specification illustrate several aspects of the disclosure and, together with the description, serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Aspects of this disclosure relate to methods employing a stencil (e.g., a biocompatible polymeric film) to improve the seeding of live cells into spatially defined regions of a substrate, such as microwells or other desired microenvironments. In certain embodiments directed to in situ stencil fabrication, a sacrificial film devoid of holes is assembled to a microwell array and holes are generated by aligning a hole generation mechanism or apparatus to the microwells to produce a stencil including holes registered with microwells. Alternatively, holes may be generated in the film first to produce a stencil, and then the stencil (film) with a pattern of holes may be aligned to the microwells. In certain embodiments, holes may be defined in a film using lasers, hot needles, or other means to form a stencil. The present disclosure is not limited to the specific methods of fabricating holes in sacrificial films disclosed herein. A film embodies a thin layer of material, and may be considered "sacrificial" in that it is subject to and/or configured for removal from an underlying feature-containing substrate. Upon generation of holes in a sacrificial film, the sacrificial film may be considered a stencil. Cells are seeded through holes defined in the stencil. Utilization of the stencil defining holes registered with microwells during cell seeding minimizes the presence of cells at microwell lips and in interstitial areas between microwells. Cell-containing microarrays may be subject to incubation. The stencil is then subject to removal and/or the cell-containing microarray may be subjected to standard array processing.

Figure 1:
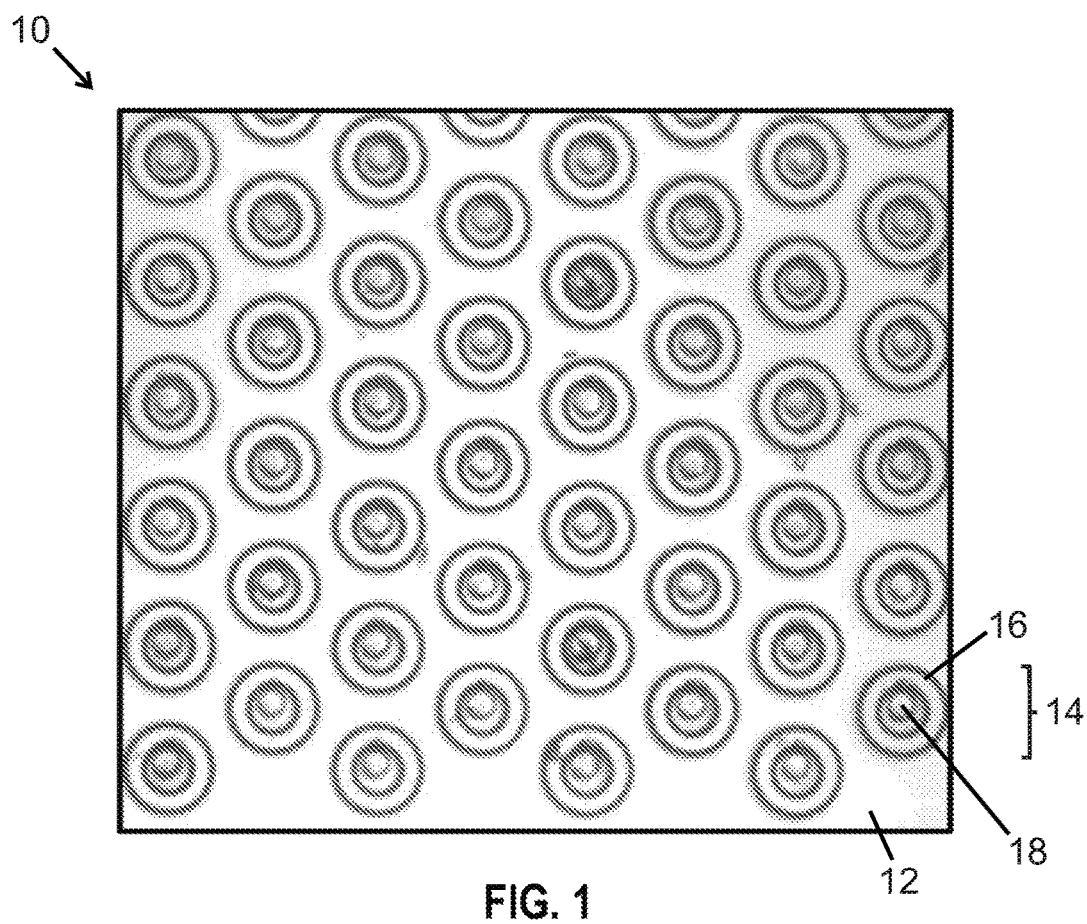
FIG. 1 is a magnified top plan view photograph of a portion of a microarray device including a substrate defining an array of microwells overlaid with a film cover including holes registered with the microwells.

FIG. 1 is a magnified top plan view photograph of a portion of a microarray device 10 including a substrate 12 defining an array of microwells 14 overlaid with a sacrificial film defining holes 18 registered with the array of microwells 16. Each microwell 14 is defined by at least one raised feature 16, such as an annular shaped wall. The holes 18 defined in the sacrificial film may be formed by any of the various methods disclosed herein.

In one embodiment, a biocompatible polymer film (preferably comprising, consisting essentially of, or consisting of low density polyethylene, polyvinyl chloride, or polyolefin) is firmly secured, under tension, over an appropriate cell seeding substrate. In certain embodiments, the film may be secured by adhesion, thermal bonding, and/or mechanical compression. The film and/or substrate preferably possesses optical or physical properties such that features of the substrate can be distinguished and referenced during manual or computerized numerical controlled alignment.

In certain embodiments, a removable cover material (e.g., fused silica) is placed into contact with a sacrificial film (used to form a stencil) such that the sacrificial film is seated between a cell seeding substrate and the cover. The cell seeding substrates defines a plurality of features (e.g., microwells) that are elevated or recessed relative to a body structure connecting the plurality of features. A laser is aligned to the appropriate feature on the cell seeding substrate (i.e., in situ alignment) while focused on the sacrificial (polymer) film. Laser emissions may be transmitted through either the cell seeding substrate or the cover to impinge on the sacrificial film. A single hole or void per feature (e.g., microwell) is defined in the sacrificial film, with each hole or void being nominally centered on the feature defined in or on the cell seeding substrate. The laser is optimized (with respect to parameters such as wavelength, pulse duration, frequency, fluence, etc.) for the specific optical properties of the cell seeding substrate, polymer film, and cover, such that the cell seeding substrate and cover are optically transparent to emissions of the laser, and the sacrificial film is optically absorptive of emissions of the laser. Optical and physical properties of the film material may be altered (tempered, plasma treated, silanized, etc.) to alter the absorptive or adhesive properties that facilitate successful hole formation.

In certain embodiments, a laser may be used to define holes in a sacrificial film arranged between a feature-defining substrate (e.g., a microarray device, such as a microwell array device) and a removable cover. At least portions of microwells of a multi-well plate may be elevated or recessed relative to a body portion of a substrate connecting the microwells. During assembly, microwells (e.g., in the multi-well plate) are overlaid with the sacrificial film and the cover, wherein the sacrificial film is absorptive of laser light and the cover is transparent to laser light. During laser assisted melting, a laser beam is directed through the transparent cover to impinge on the sacrificial film in a location registered with an underlying microwell. Such action causes a portion of sacrificial film to melt and locally adhere to the transparent cover. During separation, the cover is removed, with a locally adhered portion of the sacrificial film remaining adhered to the transparent cover, thereby yielding a hole in the sacrificial film registered with an underlying microwell. During cell seeding, cells are seeded through the hole into the microwell. Thereafter, the cells may be incubated and one or more assays (e.g., assays involving measurement of metabolic flux) may be performed. In certain embodiments, the remainder of the sacrificial film (embodying a sacrificial film) is removed from the microwell array device prior to collection of data from the assay.

Figure 2A:
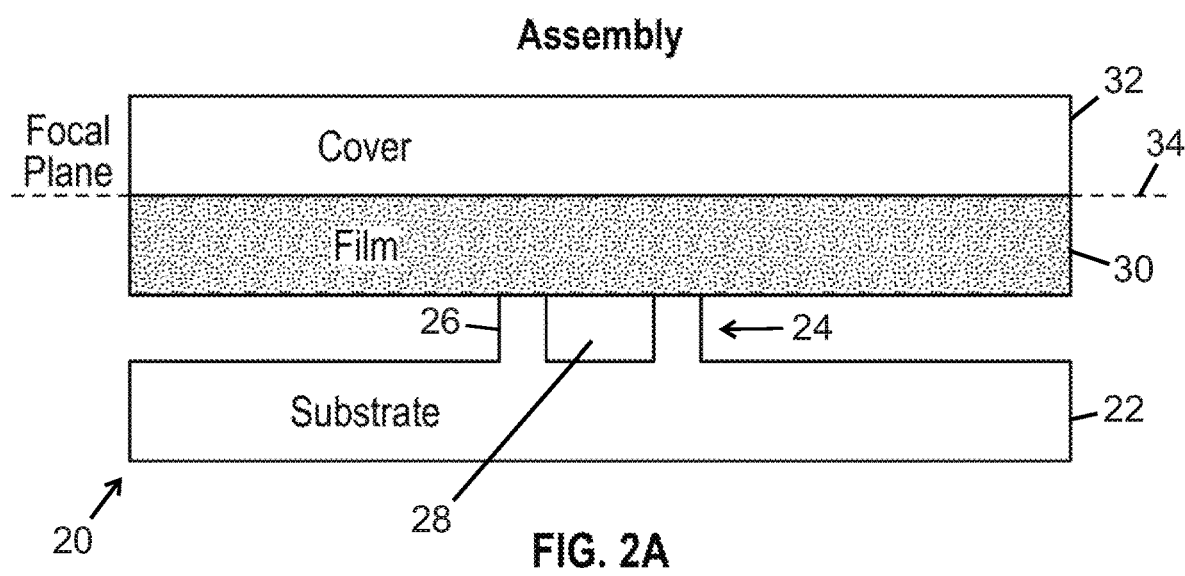
FIG. 2A is a cross-sectional schematic illustration of a portion of a microwell array device with a sacrificial film and a cover overlying a microwell thereof.
Figure 2B:
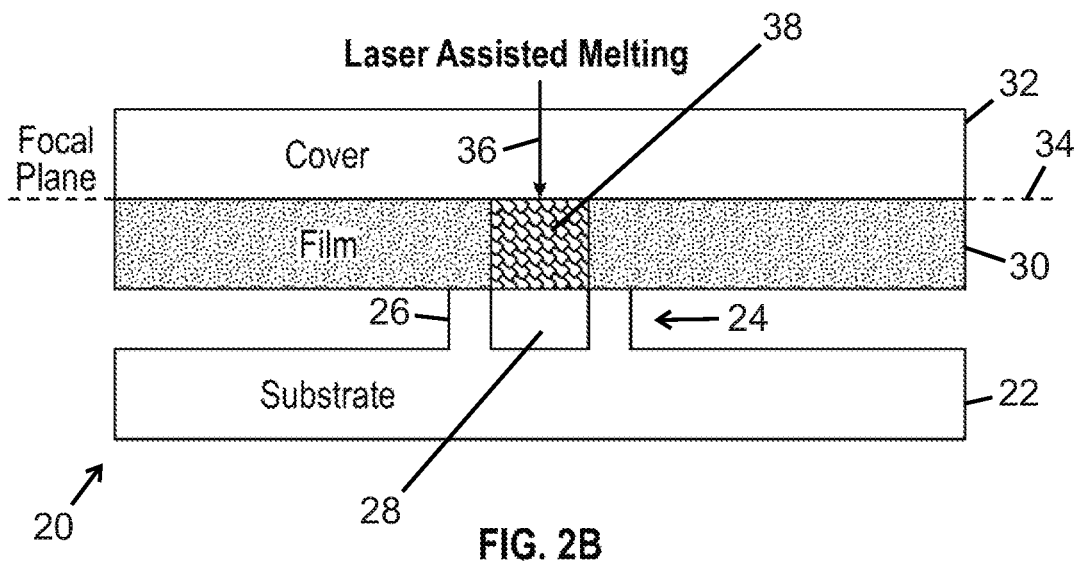
FIG. 2B is a cross-sectional schematic illustration of the microwell array device portion of FIG. 2A following impingement of a beam of laser energy on the sacrificial film to locally melt a portion of the sacrificial film and to cause the locally melted portion to adhere to the cover.

An example of a method facilitating cell seeding utilizing a sacrificial film arranged between a feature-defining substrate and a removable cover is described in connection with FIGS. 2A-2E. FIG. 2A illustrates a portion of a microwell array device 20 including a cell seeding substrate 22 having raised features 26 forming a microwell 24 defining a reservoir 28, with a sacrificial film 30 overlying and contacting a top surface of the microwell 24, and with a cover 32 overlying and contacting a top surface of the sacrificial film 30. A focal plane 34 for receiving laser energy is provided at an interface between the sacrificial film 30 and the cover 32. Although only a single microwell 24 is shown, it is to be appreciated that the microwell array device 20 may include a multitude of microwells 24 configured as an array and defined in or on the cell seeding substrate 22, with the cell seeding substrate 22 embodying a body structure connecting the microwells 24. FIG. 2B illustrates the same microwell array device portion 20 following impingement of a beam 36 of laser energy through the cover 32 on a portion of the sacrificial film 30 overlying the reservoir 28 of the microwell 24 to form a locally melted portion 38 of the sacrificial film 30. Preferably, the locally melted portion 38 of the sacrificial film 30 adheres to the cover 32 to permit the locally melted portion 38 to be removed from the remainder of the sacrificial film 30. In certain embodiments, a laser used to define holes in a sacrificial film may have a wavelength of about 355 nm, a pulse duration of from about 40 to 100 ns, a pulse frequency of about 6 kHz, and a power of about 48 uJ/pulse. In certain embodiments, one or more of the foregoing parameters may be varied by ±10%, ±7%, ±5%, ±3%, ±2%, or ±1%.

Figure 2C:
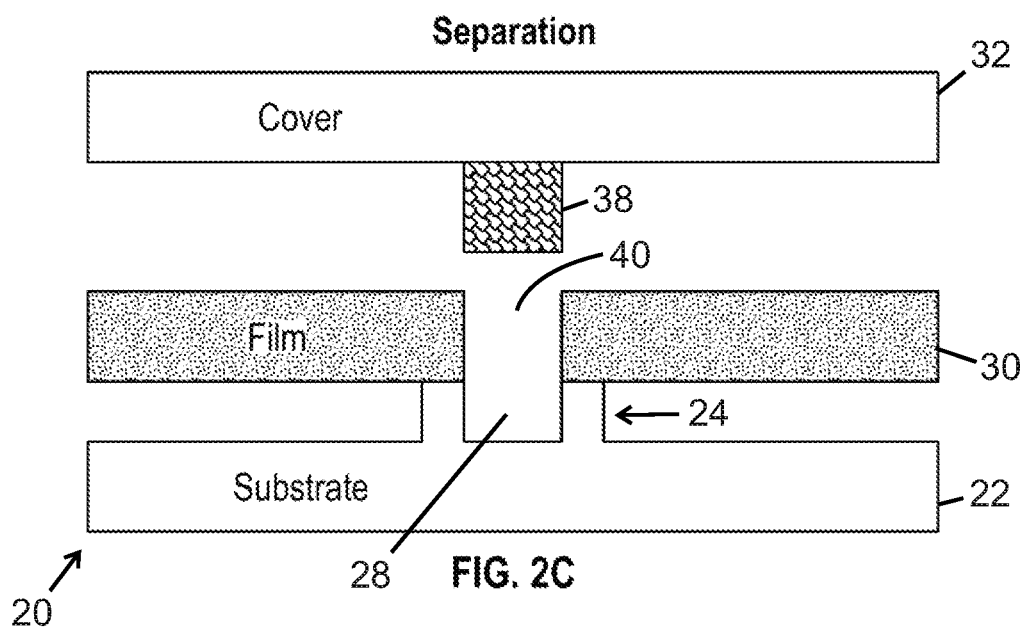
FIG. 2C is a cross-sectional schematic illustration of the microwell array device portion of FIG. 2B following removal of the cover from the sacrificial film, with the locally melted portion of the sacrificial film adhered to the cover.
Figure 2D:
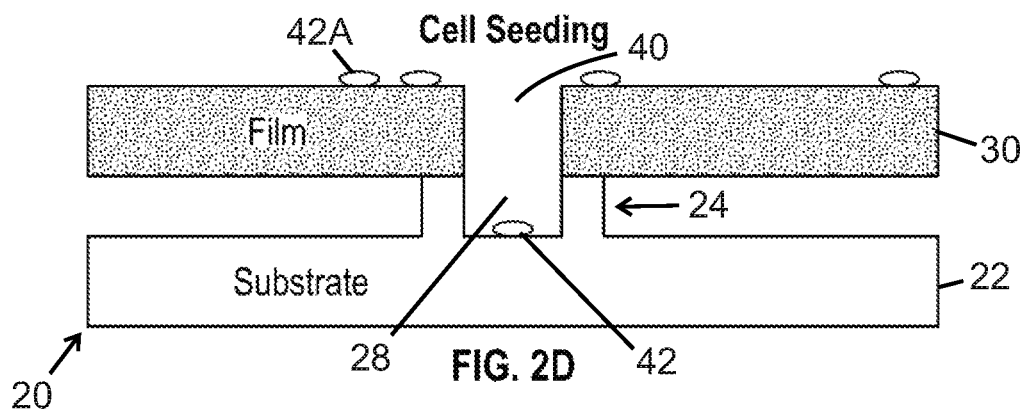
FIG. 2D is a cross-sectional schematic illustration of the microwell array device portion of FIG. 2C following application of cells over the sacrificial film and application of a single cell into a single microwell.
Figure 2E:
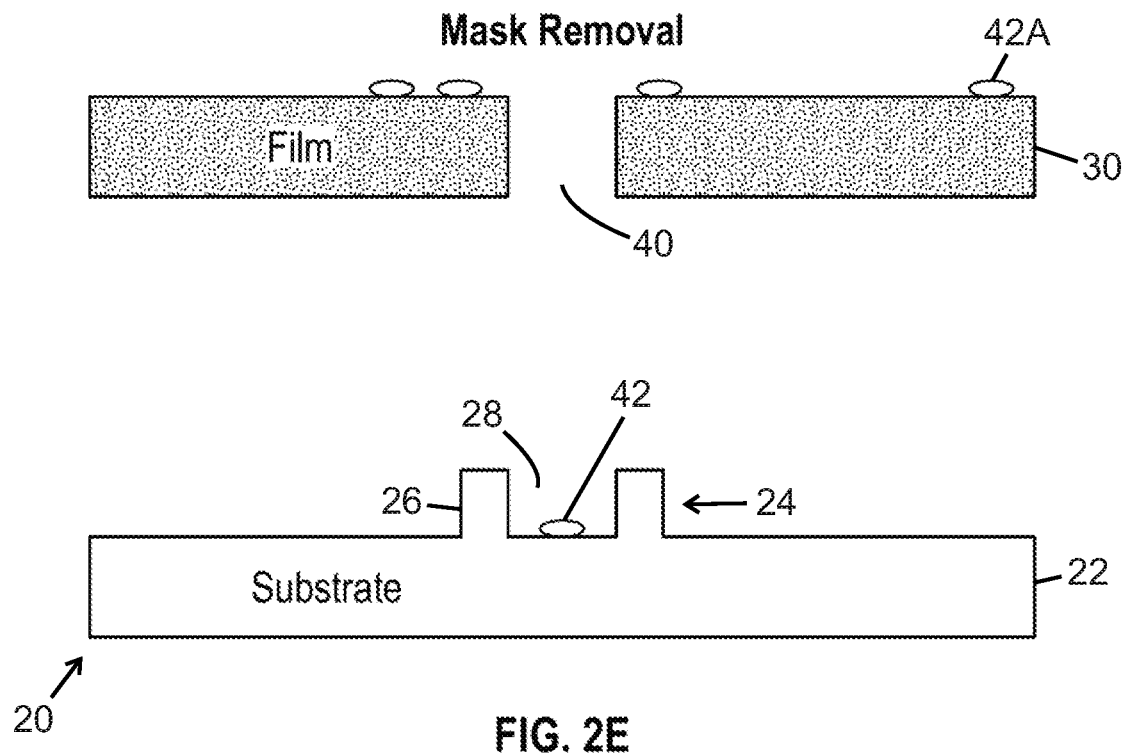
FIG. 2E is a cross-sectional schematic illustration of the microwell array device portion of FIG. 2D following removal of the sacrificial film from the microwell.

Although only a single microwell 24 is shown in FIG. 2B, it is to be appreciated that a microwell array device may include an array of multiple microwells, and the laser impingement step may be repeated for each microwell. Successful application of the laser impingement step for each microwell will result in multiple regions of the sacrificial film 30 being selectively and adherently melted onto the cover 32, with damage to the local structural integrity of the sacrificial film 30. As shown in FIG. 2C, locally melted portions 38 of the sacrificial film 30 are selectively transferred onto the cover 32, such that removal (e.g., separation) of the cover 32 causes the sacrificial film 30 secured to microwells 24 of the cell seeding substrate 22 to define a pattern of holes 40 causing the sacrificial film 30 to form a stencil, with each hole 40 being registered with a reservoir 28 of a respective microwell 24. As shown in FIG. 2D, thereafter, cell seeding is performed, causing one or more cells 42 to pass through each hole 40 defined in the sacrificial film (or stencil) 30 into a reservoir 28 of a corresponding microwell 24, and resulting in inadvertent deposition of additional cells 42A along a top surface of the sacrificial film 30. The microwell array device 20 may be subject to various processing steps (e.g., cell incubation, assaying, etc.) with or without the sacrificial film 30 remaining adhered or otherwise in contact with microwells 24 of the cell seeding substrate 22. Upon removal of the sacrificial film 30 bearing inadvertently deposited additional cells 42A as shown in FIG. 2E (e.g., "mask removal"), the microwell array device 20 includes one or more cells 42 within reservoirs 28 of microwells 24, and is devoid of cells along regions of the cell seeding substrate 22 non-coincident with the microwells 24.

Figure 5:
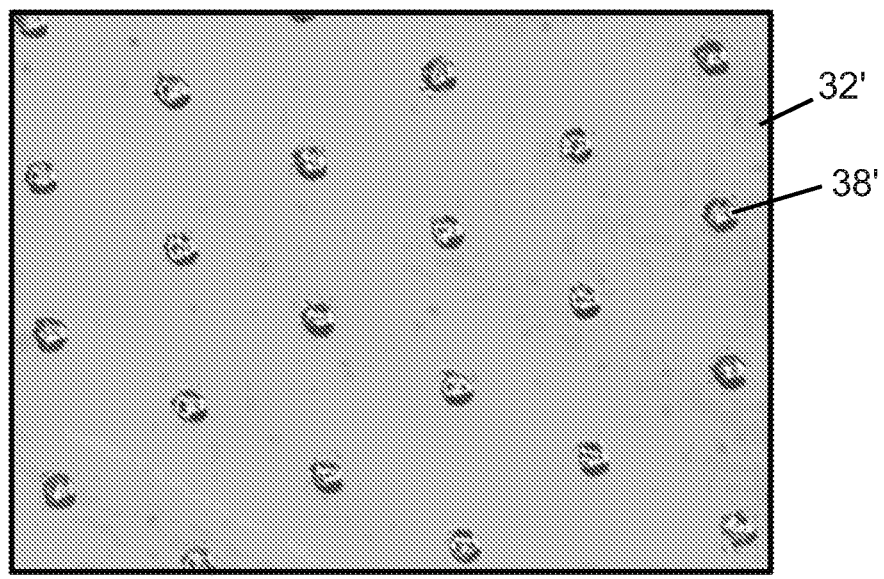
FIG. 5 is a magnified photograph of a cover glass following formation of laser assisted film transfer spots each being about 24 microns in diameter.

FIG. 5 is a magnified photograph of a cover glass 32' following formation of laser assisted film transfer spots 38' (consistent with the locally melted portions 38 illustrated in FIGS. 2B and 2C) each being about 24 microns in diameter.

Another embodiment uses a method similar to that described in connection with FIGS. 2A-2E, but omits a sacrificial cover. A film may be arranged over a feature-laden substrate (e.g., a microarray device) without an overlying cover, and laser ablation may be performed (e.g., through the substrate) to locally vaporize or otherwise thermally destroy portions of the film to form holes proximate to features (e.g., microwells) suitable for receiving cells, without causing portions of the film to be transferred (e.g., adhered) to a cover. An example of such a method is described hereinafter in connection with FIGS. 7A-7E. In some instances, residue from the laser beam may be deposited in each microwell, and may remain in the microwell after cell seeding and subsequent removal of the film. This residue has been demonstrated to be biocompatible with live cells. The residue may decrease the internal sealed volume of the microwell which is compensated during calculation of oxygen consumption rate (OCR).

In certain embodiments, methods for promoting cell seeding may employ a hot needle to define holes in a sacrificial film (e.g., polymer film). A biocompatible polymer film is first secured over an appropriate cell seeding substrate. The film and/or substrate preferably possess optical or physical properties such that features of the cell seeding substrate can be distinguished and referenced during manual or computerized numerical controlled alignment. A hot needle is brought into contact or close proximity to the film, causing a cleft to form. Tension in the film, combined with heat transfer from the needle to the film, causes a local redistribution of material, thereby expanding the cleft to the desired diameter. The film secured to the cell seeding substrate will possess a pattern of holes (e.g., voids in the film). Such a method advantageously avoids the possible deposition of bioproduct of laser ablation into microwells, and allows the use of simpler equipment for hole creation.

Figure 3A:
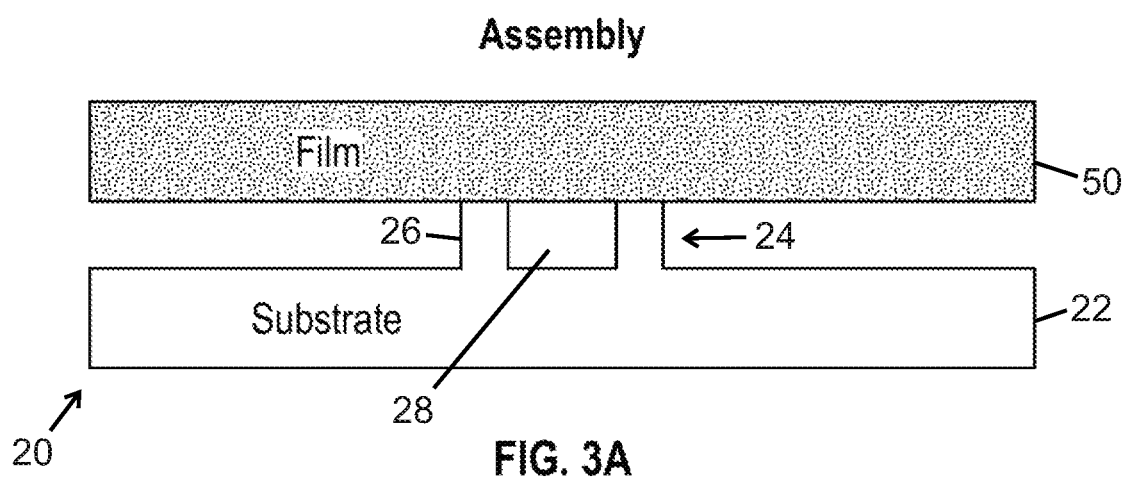
FIG. 3A is a cross-sectional schematic illustration of a portion of a microwell array device with a sacrificial film overlying a microwell thereof.
Figure 3B:
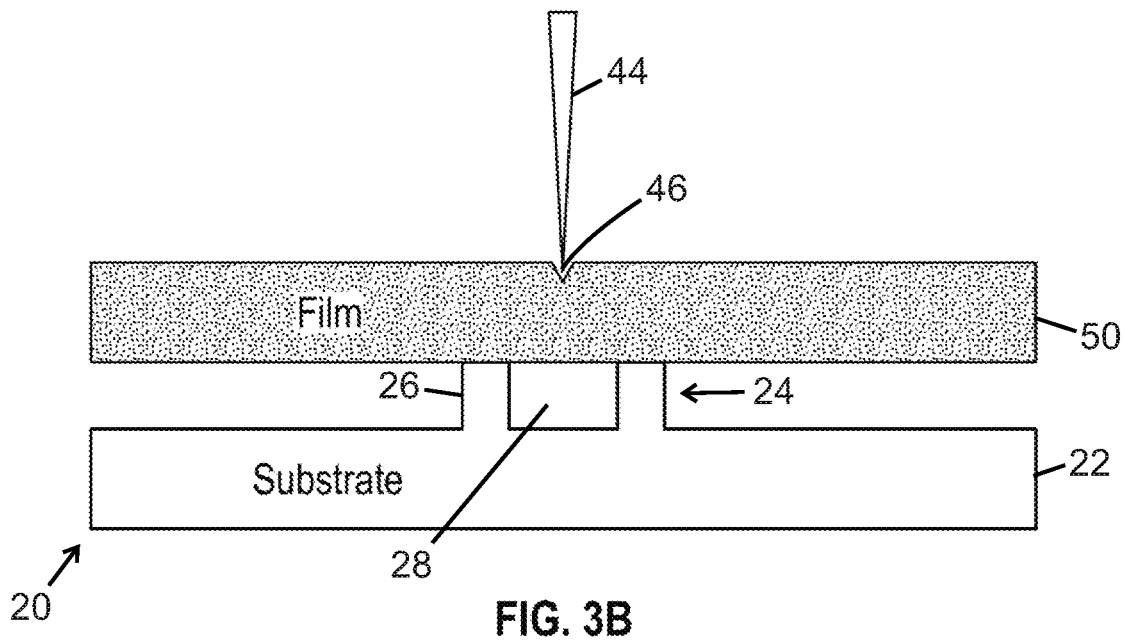
FIG. 3B is a cross-sectional schematic illustration of the microwell array device portion of FIG. 3A following initial fracture of a surface of the sacrificial film using a hot needle.
Figure 3C:
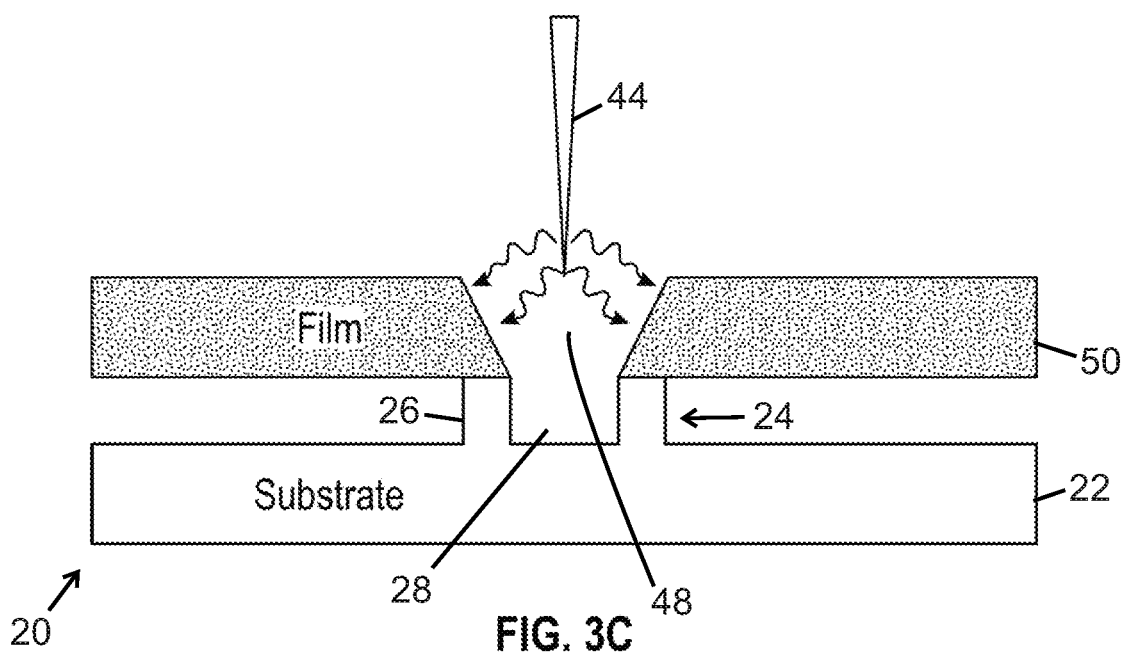
FIG. 3C is a cross-sectional schematic illustration of the microwell array device portion of FIG. 3B following thermal expansion of an opening in the sacrificial film using the hot needle.
Figure 3D:
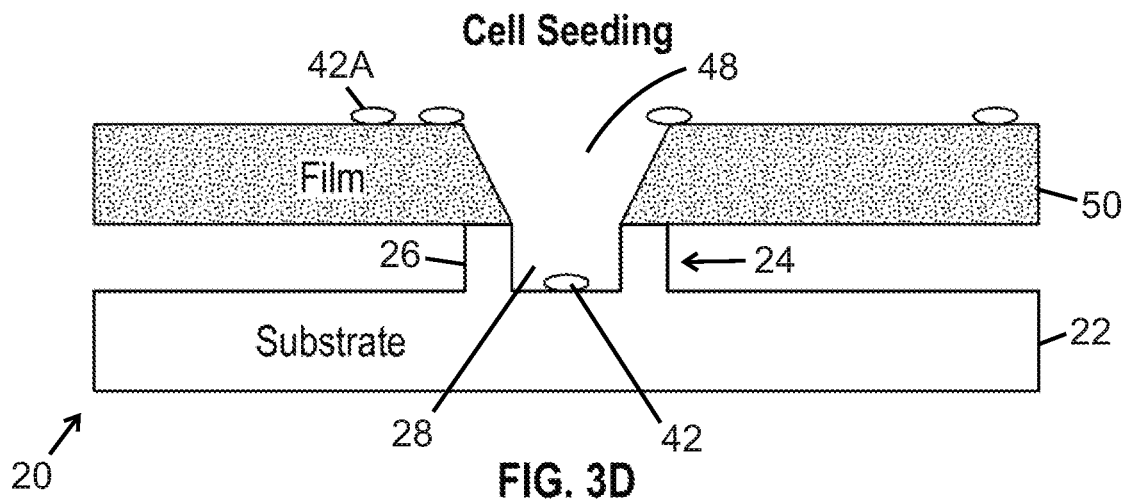
FIG. 3D is a cross-sectional schematic illustration of the microwell array device portion of FIG. 3C following application of cells over the sacrificial film and seeding of a single cell into a single microwell.
Figure 3E:
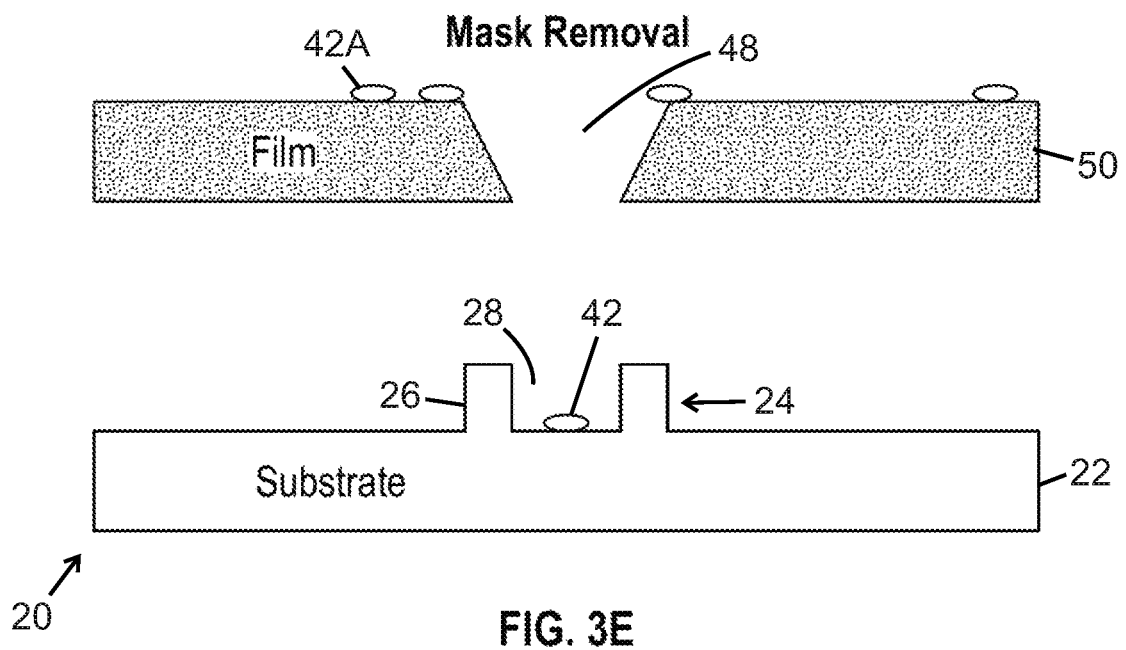
FIG. 3E is a cross-sectional schematic illustration of the microwell array device portion of FIG. 3D following removal of the sacrificial film from the microwell.

FIGS. 3A-3E schematically illustrate steps of a method for cell seeding utilizing a stencil including holes produced by a hot needle. FIG. 3A illustrates a portion of a microwell array device 20, including a cell seeding substrate 22 having raised features 26 forming a microwell 24 defining a reservoir 28, during assembly with a sacrificial film 50 overlying and contacting a top surface of the microwell 24. Although only a single microwell 24 is shown, it is to be appreciated that the microwell array device 20 may include a multitude of microwells 24 configured as an array and defined in or on the substrate 22, with the cell seeding substrate 22 embodying a body structure connecting the microwells. Referring to FIG. 3B, during film surface fracture, a hot needle 44 is directed through at least a portion of the sacrificial film 50 in a position registered with the reservoir 28 of the underlying microwell 24 to define a small cleft 46. Referring to FIG. 3C, during cleft thermal expansion, heat from the hot needle 44 causes the small cleft 46 (shown in FIG. 3B) to grow in diameter to form a hole 48. In certain embodiments, at least a portion of the expanded cleft along an upper surface of the sacrificial film 50 may extend beyond a diameter of the reservoir 28 of the underlying microwell 24, while a bottom boundary of the sacrificial film 50 remains adhered to upper surfaces of the microwell 24. Referring to FIG. 3D, using cell seeding, one or more cells 42 are seeded through the hole 48 defined in the sacrificial film 50 into the reservoir 28 of the microwell 24, while additional cells 42A are inadvertently deposited along a top surface of the sacrificial film 50. Thereafter microwell array device 20 may be subject to various processing steps (e.g., cell incubation, assaying, etc.) with or without the sacrificial film 50 remaining adhered or otherwise in contact with microwells 24 of the cell seeding substrate 22. Possible assays include assays involving measurement of metabolic flux. In certain embodiments, the sacrificial film 50 is removed from the microwell array device 20 prior to collection of data from the assay. Upon removal of the sacrificial film 50 bearing inadvertently deposited additional cells 42A as shown in FIG. 3E, the microwell array device 20 includes one or more cells 42 within reservoirs 28 of microwells 24, and is devoid of cells along regions of the cell seeding substrate 22 non-coincident with the microwells 24.

Figure 4:
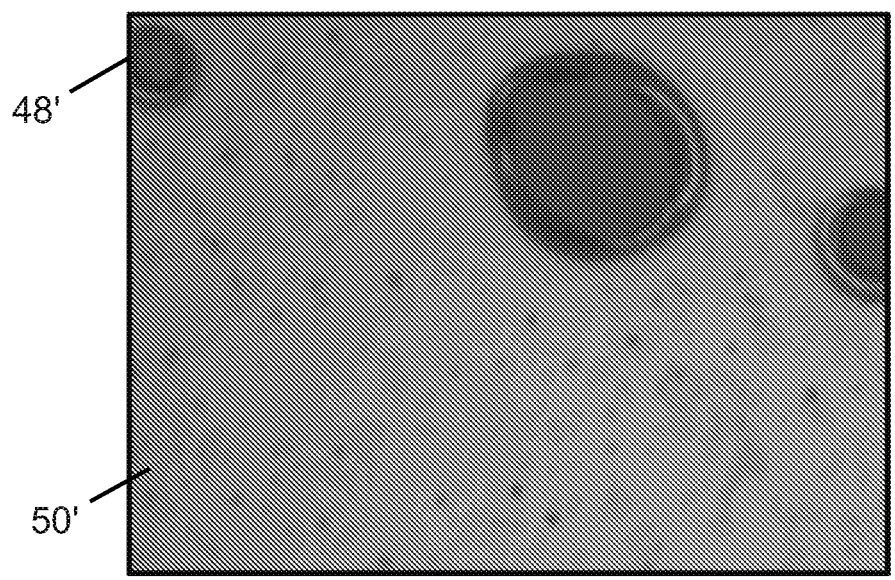
FIG. 4 is a magnified photograph of a portion of a microwell array device including a sacrificial film stencil defining hot needle holes, with a top left hole being about 3.9 microns in diameter.

FIG. 4 is a magnified photograph of a portion of a microwell array device including a sacrificial film stencil 50' defining hot needle holes, with a top left hole 48' being about 3.9 microns in diameter.

In another embodiment, a biocompatible polymer film (e.g., polyimide) with laminated acrylic pressure-sensitive adhesive (PSA) is attached, face side, to a glass sacrificial cover (e.g., a microscope slide). A laser may be used to create a pattern of holes corresponding to the hole pattern of a microwell array, but with the laser-fabricated holes having diameters smaller than the microwell inside diameter. To accomplish this, in a similar manner as described above, the polymer film may be selectively and adherently melted onto a cover, and the hole features thereby selectively transferred onto the cover. For this subsequent-alignment case, the patterned polymer film is then removed (with residual hole material attached to the cover) and attached (back side) to a vacuum chuck. The chuck, holding the film, is then brought into close proximity to the microwell array, aligned using microscopy, and finally brought together under pressure to enable adhesion. The vacuum is released and the chuck removed. The film secured to the cell seeding substrate (defining microwells) will possess a pattern of film voids aligned to microwells. This method has the following advantages: stencil film parts can be processed in batch mode without pre-attachment to the microwell array; and stencil fabrication can be performed without the need for cleanroom processing, provided the stencil is subsequently cleaned.

Figure 6:
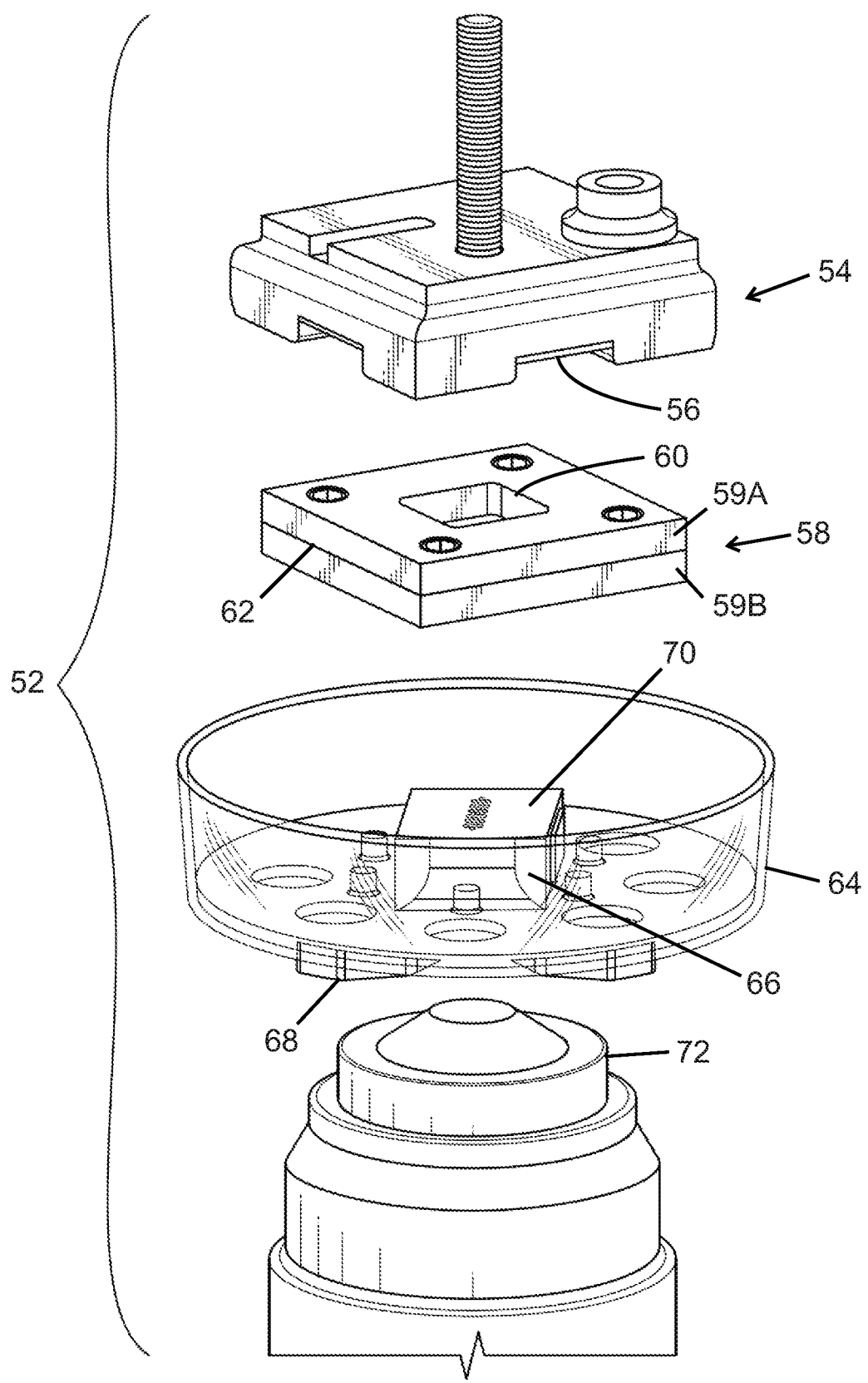
FIG. 6 is an exploded perspective view schematic illustration of elements of a magnetic cell-seeding stencil alignment fixture.

In another embodiment, a biocompatible film (e.g., polyimide) or thin (e.g., 50 μm) stainless steel substrate, without adhesive, is processed with a laser to create a pattern of holes corresponding to holes of a microwell array, similar to the laser hole-defining method described above. The stencil is preferably tensioned to ensure that it is flat and rigid. FIG. 6 is an exploded perspective view schematic illustration of elements of a magnetic cell-seeding stencil alignment fixture 52. A preferred method for tensioning a stencil 62 is to pre-heat the stencil 62 to about 50° C., then clamp the stencil 62 between two halves 59A, 59B of a magnetic stainless steel frame 58 at room temperature (e.g., 25° C.), then allow it to cool. If the stencil material has a higher coefficient of thermal expansion than the magnetic stainless steel frame 58, then both the stencil 62 and the magnetic stainless steel frame 58 could be pre-heated, then clamped, and then cooled to provide stencil tension. An array of rare-earth magnets 68 may be attached to the interior (bottom) surface of a biocompatible container 64 (e.g., a petri dish) in such a manner so as to not occlude microscope optics 72. A custom-fabricated array holder 66 may be placed inside the container 64 for holding a microwell array device 70 centered and elevated. The magnetic stainless steel frame 58, which defines an aperture 60 through which the clamped stencil 62 is exposed, is attached to a vacuum chuck 54, which includes a sealing gasket 56 along a lower surface thereof. The vacuum chuck 54 in combination with the magnetic stainless steel frame 58 and clamped stencil 62, is then brought into close proximity to the microwell array device 70, aligned using microscopy (e.g., using microscope optics 72), and finally brought into contact with the microwell array device 70. Vacuum is released from the vacuum chuck 54 and the vacuum chuck 54 is removed. The magnetic stainless steel frame 58 and stencil 62 are held in position by magnetic attraction between the rare-earth magnets 68 and the magnetic stainless steel frame 58. After performance of a final assay step, the magnetic stainless steel frame 58 and the stencil 62 can be sterilized (e.g., via autoclave) for re-use. This method has the following advantages: the stencil can be reused; and stencil fabrication can be performed without the need for cleanroom processing, provided the stencil is subsequently cleaned.

For all of the above methods, the assembly of a microwell array and a hole-defining sacrificial film may be exposed to plasma treatment, and then soaked in cell medium, with air being displaced from the microwells. Air displacement can be enhanced with any of several standard methods, including elevated temperature and carbon dioxide substitution. Cells may then be randomly seeded and incubated to allow attachment, according to a standard process. Then the patterned stencil is removed, along with unwanted cells attached to the stencil, while leaving cells in microwells of the microarray. The microarray with cells may then be further processed according to standard procedures, such as assembly with a sensor lid for metabolic flux analysis.

Figure 7:
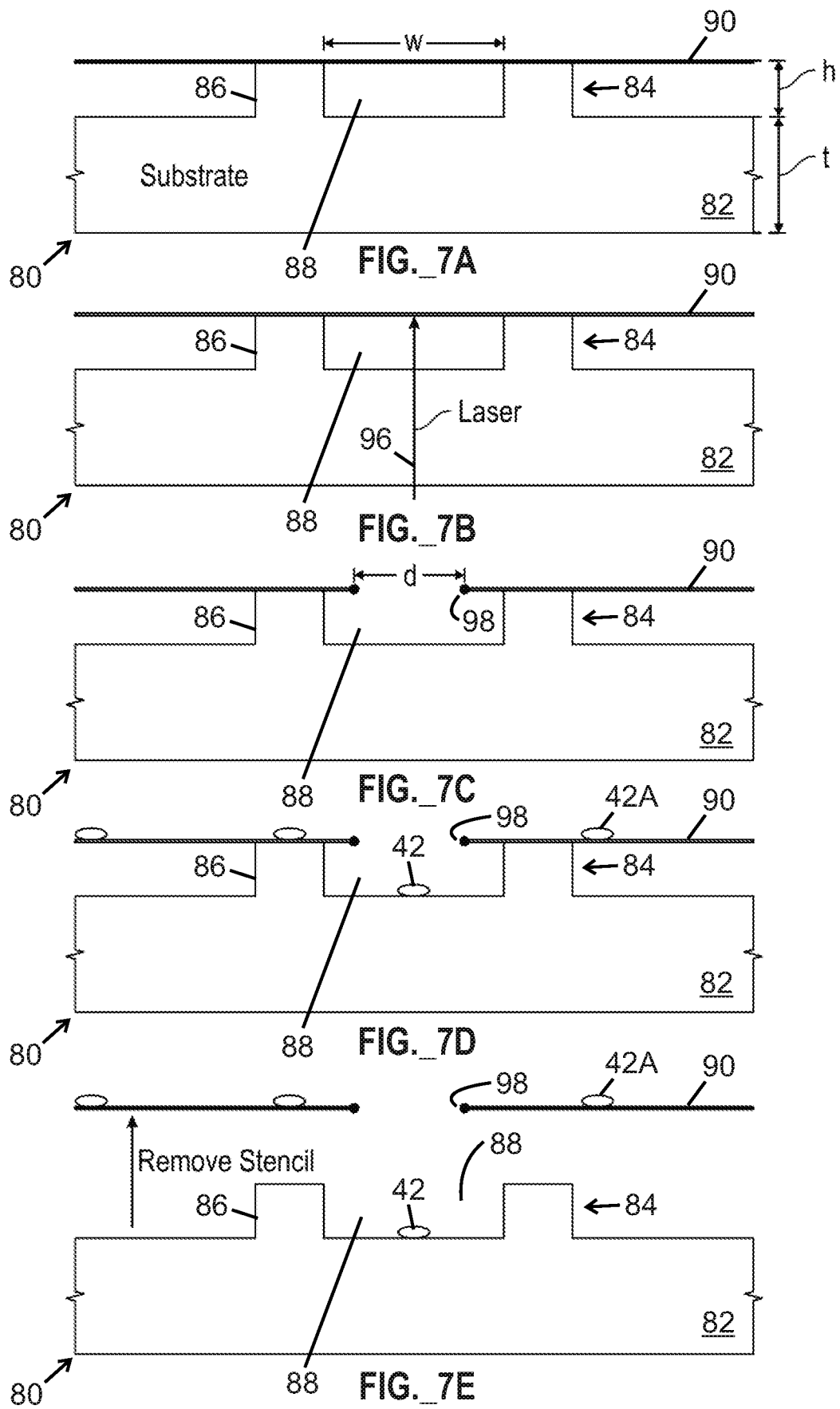
FIG. 7A is a cross-sectional schematic illustration of a portion of a microwell array device with a sacrificial film overlying a microwell thereof.
FIG. 7B is a cross-sectional schematic illustration of the microwell array device portion of FIG. 7A following transmission of a beam of laser energy through a substrate of the microwell array device to impinge on the sacrificial film.
FIG. 7C is a cross-sectional schematic illustration of the microwell array device portion of FIG. 7B showing formation of a hole in the sacrificial film due to impingement of laser energy.
FIG. 7D is a cross-sectional schematic illustration of the microwell array device portion of FIG. 7C following application of cells over the sacrificial film and seeding of a single cell into a single microwell.
FIG. 7E is a cross-sectional schematic illustration of the microwell array device portion of FIG. 7D following removal of the sacrificial film from the microwell.

Steps for promoting cell seeding utilizing a sacrificial film with holes defined by a laser, without transferring locally melted portions of the film to a cover, are described in connection with FIGS. 7A-7E. FIG. 7A illustrates a portion of a microwell array device 80 including a cell seeding substrate 82 having raised features 86 forming a microwell 84 defining a reservoir 88, with a sacrificial film 90 overlying and contacting a top surface of the microwell 84. Although only a single microwell 84 is shown, it is to be appreciated that the microwell array device 80 may include a multitude of microwells 84 configured as an array and defined in or on the substrate 82, with the substrate 82 embodying a body structure connecting the microwells 84. As shown, the body structure of the substrate 82 has a thickness t, and the raised features 86 forming microwells 84 have a height h, wherein the height h is preferably substantially smaller than the thickness t. In one example, the height h may be about 20 microns, and the thickness t may be about 500 microns. The reservoir 88 of the microwell 84 further includes a width w. FIG. 7B illustrates the same microwell array device portion 80 during transmission of a beam 96 of laser energy through the body portion of the substrate 82 to impinge on a portion of the sacrificial film 90 overlying the reservoir 88 of the microwell 84. Referring to FIG. 7C, the beam 96 of laser energy (shown in FIG. 7B) preferably ablates (e.g., vaporizes) a portion of the sacrificial film 90 to define a hole 98 having a diameter d and being registered with the reservoir 88 defined by the microwell 84. In certain embodiments, the beam 96 of laser energy has a peak wavelength of about 355 nm, and may be applied in one or more pulses about 500 ms in duration. Preferably, the diameter d of the hole 98 is smaller than the width w of the reservoir 88 defined by the microwell 84. In certain embodiments, the diameter d may be in a range of 40% to 95% of the width w. In one example, the width w may be about 80 microns, and the diameter d may be about 35 microns. It is to be appreciated that multiple holes 98 may be formed by repeating the laser impingement step, thereby defining a pattern of holes 98 causing the sacrificial film 90 to form a stencil, with each hole 98 being registered with a different microwell 84 of the microwell array device 80. Thereafter, cell seeding is performed. As shown in FIG. 7D, cell seeding causes one or more cells 42 to pass through each hole 98 defined in the sacrificial film (or stencil) 90 into the reservoir 88 of the corresponding microwell 84, and resulting in inadvertent deposition of additional cells 42A along a top surface of the sacrificial film 90. The microwell array device 80 may be subject to various processing steps (e.g., cell incubation, assaying, etc.) with or without the sacrificial film 90 remaining adhered or otherwise in contact with microwells 84 of the substrate 82. Upon removal of the sacrificial film 90 bearing inadvertently deposited additional cells 42A as shown in FIG. 7E, the microwell array device 80 includes one or more cells 42 within reservoirs 88 of microwells 84, and is devoid of cells along regions of the substrate 82 non-coincident with the microwells 84.

Various samples of microwell array devices were fabricated and utilized in conjunction with a sacrificial film for cell seeding (consistent with array device design and the method steps disclosed in connection with FIGS. 7A-7E), as described below.

Fused silica wafers (4 inch diameter, 500 µm thickness) were etched using standard photolithography to create 37 arrays of 2980 microwells (20 µm deep, 80 µm inner diameter, and 120 µm outer diameter) hexagonally packed within 9 mm by 9 mm footprints. The wafer was partitioned into the 37 individual microwell array cell-seeding substrates using a dicing saw. The substrates were sonicated for 30 minutes in 1X alkaline detergent to remove particles and fibers, followed by rinsing and sonicating in deionized water for an additional 30 minutes. Substrates were then dried in a 105° C. oven and stored for later use.

Figure 8:
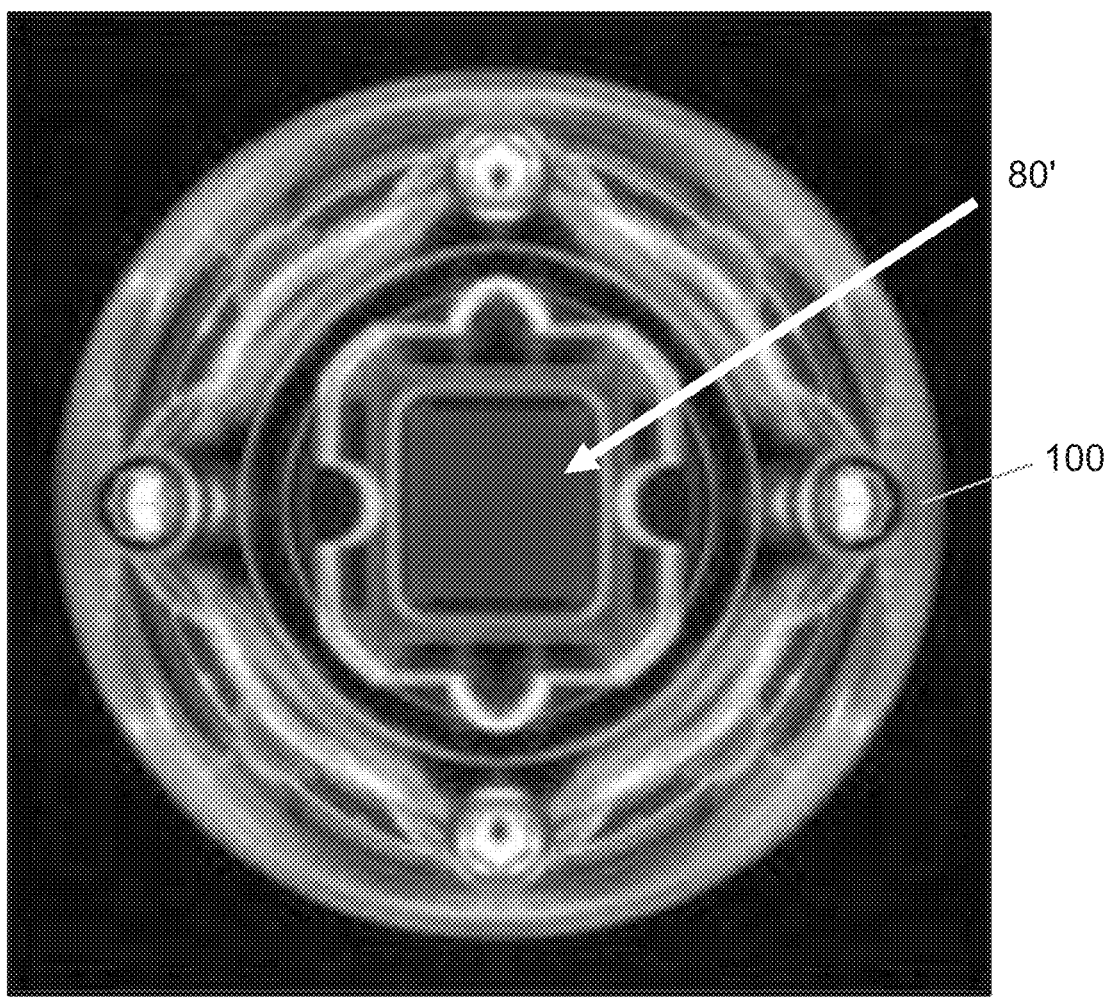
FIG. 8 is a photograph of a portion of a laser perforation and cell seeding fixture into which a microwell array is received.

X-Ray Fluorescence (XRF) film (3090, Chemplex, Palm City, Fla.) was stretched using an XRF sample cup, rinsed with ethanol, dried with nitrogen, and secured to the surface of the microwell array substrate. A laser perforation and cell seeding fixture 100 (as shown in FIG. 8) was used to clamp the polymer film onto the microwell array device 80' and also to provide a reservoir for holding cell culture medium during equilibration and cell seeding. The area of the reservoir footprint onto which cells were seeded was 236 mm². The fixture 100 ensured that positions of the film and the underlying microwell array device 80' were fixed relative to one another through the fabrication and cell seeding process. The fixture 100 was secured to the mechanical stage (ATS250, Aerotech, Pittsburgh, Pa.) of a laser fabrication environment where a 355 nm UV laser (AVIA 355-3000, Coherent, Santa Clara, Calif.) was focused through the microwell array device 80' and onto the surface of the polyester XRF film. The laser was tuned to output radiation below the ablation threshold of fused silica (48 µJ/pulse, 40 ns pulse width, 6 kHz repetition rate, defocused to 30 µm) to avoid ablation of the microwell array device 80', while still having sufficient energy to form a pore in the XRF polymeric film. Poration (i.e., hole formation) was achieved through the redistribution of film away from the site of exposure (through ablation or heat-induced polymer restructuring) leaving a pore slightly larger than the irradiated area (~35 µm). The fabrication environment was programmed to traverse the geometry of the microwell array device 80', aligning to the center of each microwell and perforating the sacrificial film using 500 ms UV laser exposures. The porated film/substrate assembly was then placed into a 35 mm petri dish and plasma treated to hydroxylate the surface of the microwell array device 80' and the XRF polymeric film, to sterilize the cell seeding surface, and to promote cell adhesion.

Before describing cell seeding steps, steps employed in culturing cells prior to seeding are described below. Cells were purchased from ATCC (Manassas, Va.). MDA-MB-231 (triple negative, metastatic breast cancer, HTB-26) were grown in DMEM supplemented with 10% FBS, 100 units/mL penicillin, and 100 μg/mL streptomycin; HME1 (derived from non-cancerous human breast epithelium, CRL-4010) were grown in MEBM supplemented with 100 units/mL penicillin, 100 μg/mL streptomycin, and supplement and growth factor kit supplied by the manufacturer (Lonza Basel, Switzerland, CC-3151, CC-4136); and K562 (chronic myelogenous leukemia, CCL-243) were grown in RPMI supplemented with 10% FBS, 100 units/mL penicillin, and 100 μg/mL streptomycin. All cultures were maintained in a 37° C. humidified incubator. Adherent cells were collected by trypsinization and all cells were counted and viability assessed with a Countess® Automated Cell Counter (Life Technologies) using the Trypan Blue dye exclusion assay. Cells were only used if initial viability was >95%.

Figure 9A:
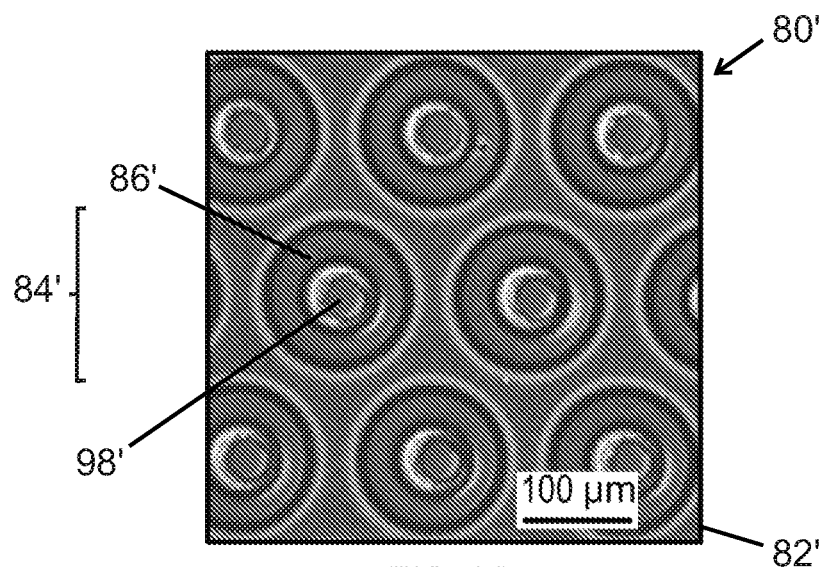
FIG. 9A is a top plan view phase contrast image of a portion of a microwell array device overlaid with a sacrificial film including holes defined therein with laser energy and registered with microwells, prior to cell seeding.
Figure 9B:
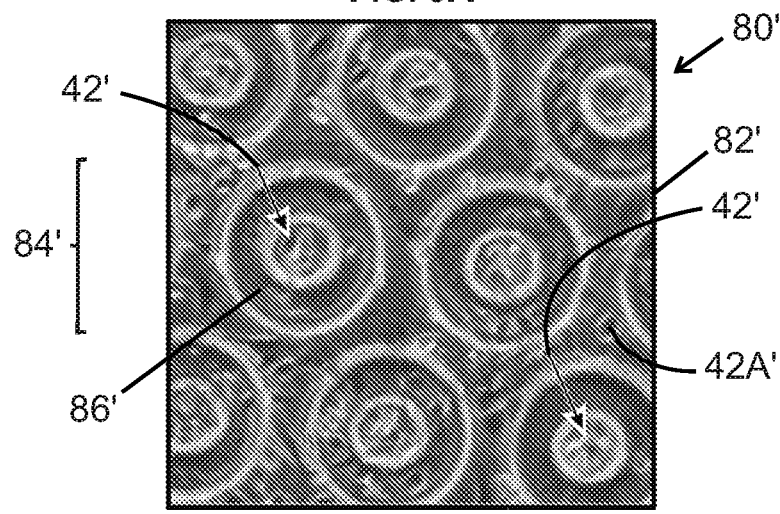
FIG. 9B is a top plan view phase contrast image of the microwell array device portion and sacrificial film of FIG. 9A following seeding of cells.

Cell seeding steps will now be described. Prior to use, plasma treated fixtures were equilibrated with cell culture medium at 37° C. for 4-18 hours. Medium was then removed by pipetting and 600 μL of cell suspension at the indicated concentration was added to the reservoir. Cells were allowed to adhere to the substrate for 18 hours under normal culture conditions. Then the fixtures were disassembled and the stencil film was peeled off with forceps, effectively removing cells not localized to interior reservoirs of microwells. The disassembled fixtures were disinfected with 70% ethanol, rinsed three times with dH$_2$O, then air dried for reuse. The stencil films were discarded after a single use. Substrates were visually inspected prior to cell seeding to verify that the stencil and microwell array were well-aligned. To demonstrate such alignment, see FIG. 9A, which shows a portion of a microwell array device 80' overlaid with a sacrificial film including holes 98' defined therein with laser energy and registered with microwells 84' of a cell seeding substrate 82', prior to cell seeding. A second visual inspection was performed after cell seeding but prior to removing the sacrificial film stencil (in the state as shown in FIG. 9B) to qualitatively evaluate cell health and morphology on the sacrificial film stencil, and within the microwells 84'. Cells 42' are contained in reservoirs bounded by raised features 86' of various microwells 84'. Additional cells 42A' are arranged atop the sacrificial film stencil in interstitial areas between microwells 84', and may be removed with the sacrificial film stencil.

A similar procedure was used to assemble "no-stencil" control assay devices, in which a microwell array substrate was placed atop the polymer film inside the fixture. Cells were then seeded into reservoirs of the uncovered substrate.

Cell labeling and imaging will now be described. Cell viability was evaluated by LIVE/DEAD® Cell Imaging Kit (488/570) (Thermo Scientific, R37601) according to the manufacturer's protocol. Cells were labeled after the 18 hour adhesion period and prior to removal of the seeding stencil. In order to evaluate the distribution of cells on the microwell array substrate, cell nuclei were labeled with the NucBlue® Live ReadyProbes® Reagent (Thermo Scientific, R37605) (FIG. 1i). The fixtures were disassembled and the stencil film removed as described, then the microwell array substrates were transferred to a six well plate containing fresh cell culture medium and the nuclear label. Cells were incubated for 10 minutes and then imaged via wide-field microscopy. The microwell array was imaged by phase contrast and the nuclear and viability stains were imaged via wide-field epi-fluorescence. The excitation and emission wavelengths (in nm) were: 360/460 to detect nuclei, 485/540 to detect live cells (green), and 540/600 to detect dead and dying cells (red). All images were collected using an inverted Nikon TE2000-U fluorescence microscope with a 4× plan apo lens, NA=0.2, and a Hamamatsu Orca Flash 4.0 digital CMOS camera. The entire microarray was imaged in each channel by stitching individual image fields. Image acquisition was automated using NIS-Elements software.

Figure 9C:
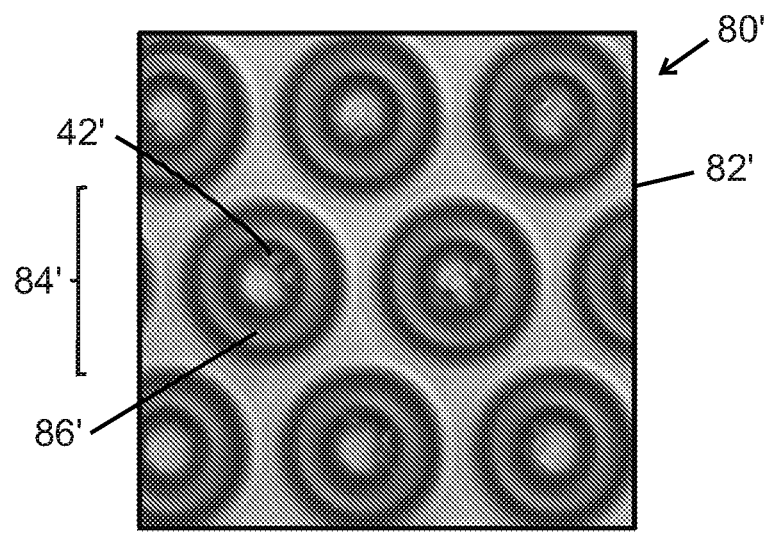
FIG. 9C is a top plan view composite fluorescence image of cell nuclei and phase contrast image of the microwell array device portion of FIG. 9B following removal of the sacrificial film.

For image analysis, cell viability and localization were evaluated by counting cells from 400 microwells from each microwell array. The 400 microwells are a randomly sampled subset from the total of ~2980 well detections provided by a normalized 2D cross correlation algorithm implemented in National Instruments LabVIEW software. For cell distribution, labeled nuclei were identified as localized to the interior or the exterior of each microwell. The exterior of the microwell was defined as the outside of the microwell or the lip of the microwell. Cells located outside of microwells were automatically assigned to the nearest microwell by comparing the Euclidean distances between the cell and the centroids of the 400 sampled microwells. The efficacy of the cell patterning stencil was evaluated by calculating the localization efficiency, which was defined as the percentage of cells localized to the interior of microwells relative to the total cell count. The biocompatibility of the polymer stencil and the stencil removal process was evaluated by examining the viability of cells in microwells, seeded with or without a stencil. Dead (or dying cells) were determined as the percent of red-labeled cells relative to total (blue) nuclei. Live cells were visually confirmed by the presence of green-labeled cytoplasm, however, this label was not used for quantification. FIG. 9C is a top plan view composite fluorescence image of cell nuclei and phase contrast image of the portion of the microwell array device 80' of FIG. 9B following removal of the sacrificial film, showing cells 42' arranged within raised features 86' of a microwell 84', without presence of cells in interstitial areas of substrate 82' between microwells 84'.

Data were pooled from a minimum of three independent experiments. Data were analyzed by Student's t-test and Mann-Whitney U test using the R statistical computing environment. P-values of <0.05 were considered significant.

Figure 10:
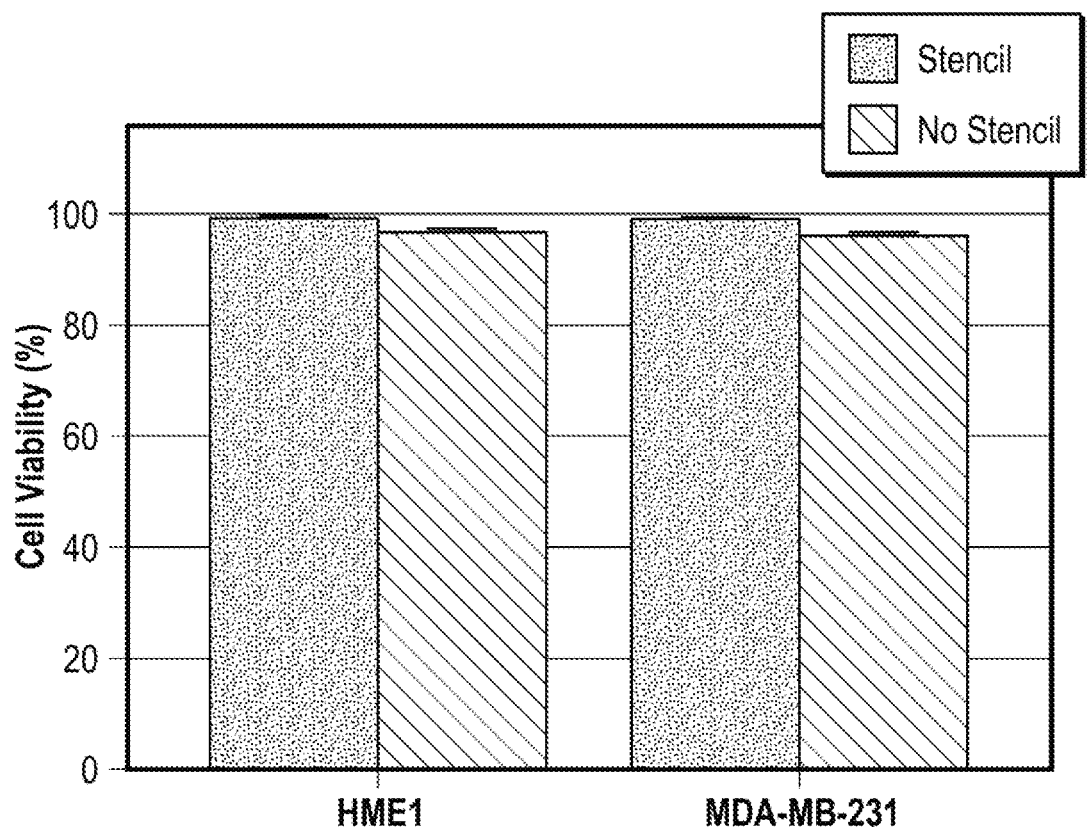
FIG. 10 is a bar graph depicting cell viability percentage for MDA-MB-231 (metastatic breast cancer) cells seeded with and without a sacrificial film stencil and HME1 (non-cancerous breast epithelium-derived) cells seeded with and without a sacrificial film stencil.

To investigate biocompatibility of the polymeric film used as the laser fabricated sacrificial film stencil, a commercially available cell viability assay was used. Viability of cells seeded through the stencil was compared to cells seeded directly onto an uncovered microwell array. Biocompatibility was measured in terms of cell viability, defined as the percentage of cells within microwells that were neither dead nor dying, as indicated by absence of red labeling of the nuclei. Cells were manually counted in blue (all nuclei) and red fluorescent images. Use of the laser-fabricated sacrificial film stencil did not reduce cell viability in either cell line. For both the stencil and no-stencil seeding environments, cell viabilities were found to be in excess of 95% on average across all experimental seeding densities, as shown in FIG. 10.

Figure 11:
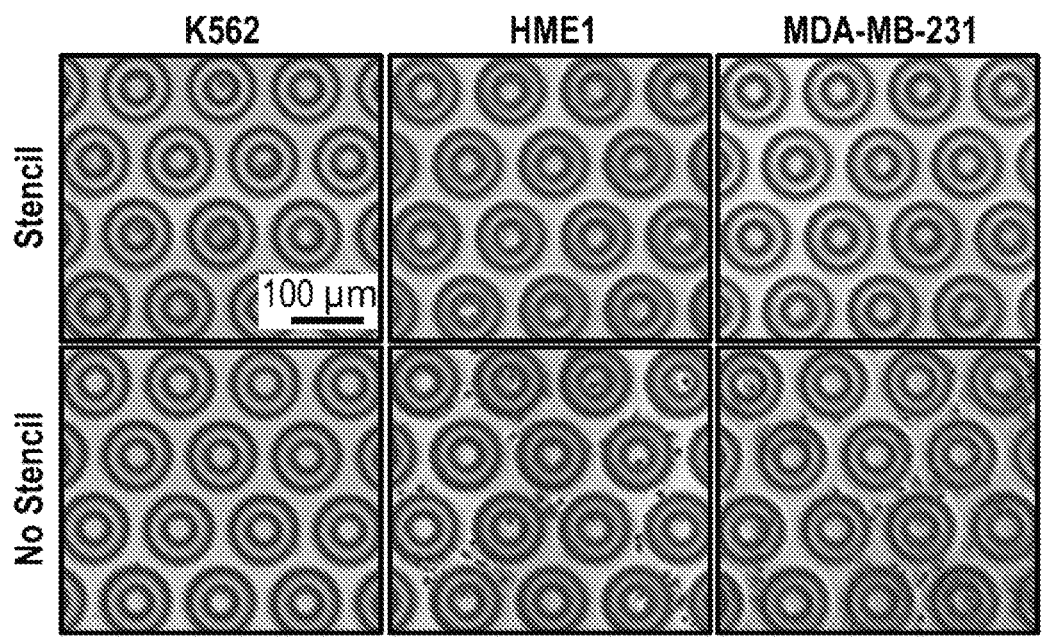
FIG. 11 provides six composite fluorescent (cell nuclei) and phase contrast (microwells) micrographs of K562 (leukemia) cells, HME1 cells, and MDA-MB-231 cells, each seeded with and without a sacrificial film stencil.
Figure 12:
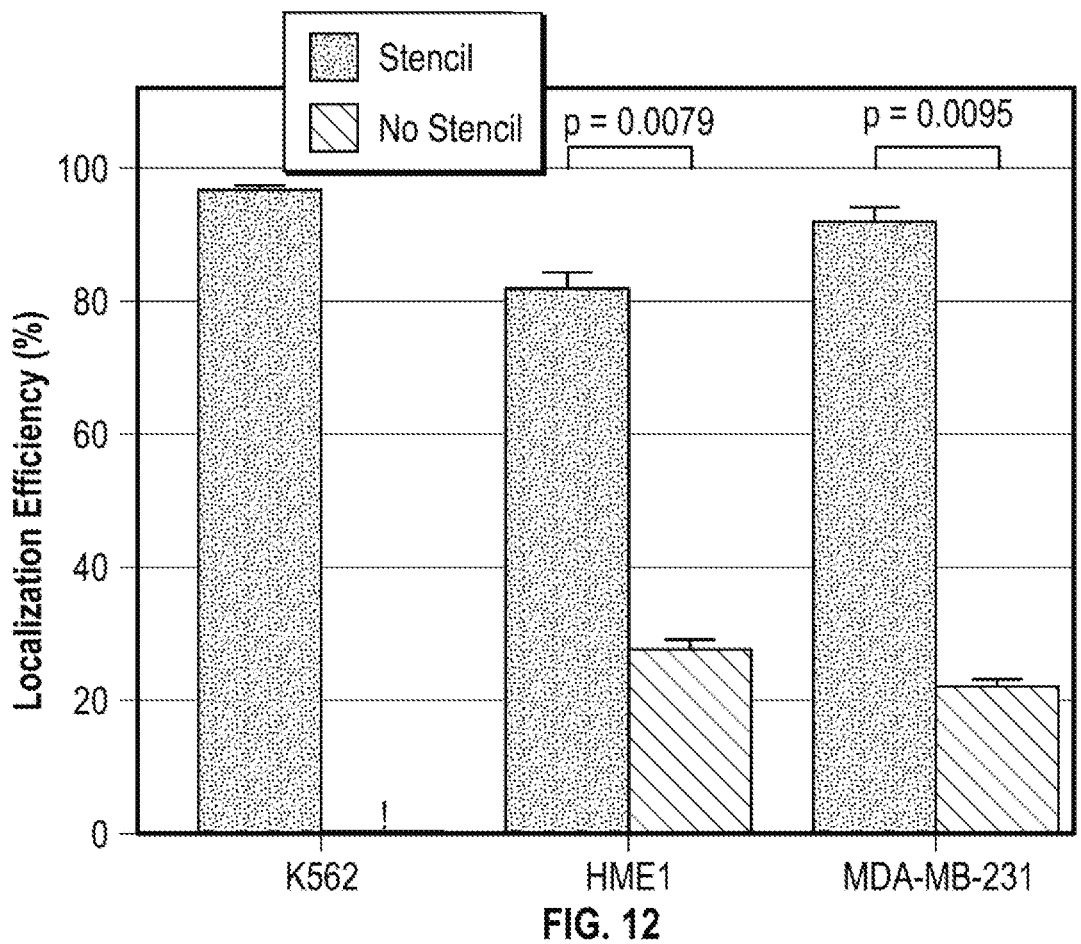
FIG. 12 is a bar chart of localization efficiency (percentage) for K562 cells seeded with a sacrificial film stencil, and for HME1 cells and MDA-MB-231 cells each seeded with and without a sacrificial film stencil.

To evaluate the effectiveness of the cell patterning stencil for localizing cells, localization efficiencies were compared between stencil-seeded and directly-seeded substrates. Cells seeded at 100K cells/mL through a stencil were highly localized to well-interiors (as shown in FIG. 11) with localization efficiencies of 97% for K562 cells, 82% for HME1 cells, and 92% for MDA-MB-231 cells. The stencils increased the percentage of cells in microwells by approximately 3-fold and 4-fold for HME1 and MDA-MB-231 cells, respectively. This represents a significant increase in localization efficiency ($p<0.01$) relative to controls seeded without stencils (as shown in FIG. 12). Seeding through the stencil had an even more profound effect on the cell distribution of K562 cells. This cell line is generally considered non-adherent and is grown in suspension culture. As expected, when these cells were seeded onto bare microwell array substrates, few cells were observed after the substrate was removed from the fixture and placed in fresh medium in a petri dish. Generally, 0-5 cells were observed across the entire array. When these cells were seeded through the stencil, many cells were retained in the microwells after removal of the stencil and transfer to fresh medium. The mechanism for this retention is not completely clear, but one possibility is that the stencil reduces turbulence of the medium close to the substrate surface. With this reduction in fluid motion, a very low level of adhesion to the substrate is sufficient to immobilize the cells in the microwells. It should be noted that although they are retained through the disassembly of the fixture and the transfer to fresh medium, rinsing these cells with moderate force, or multiple medium changes, will dislodge them.

Figure 13:
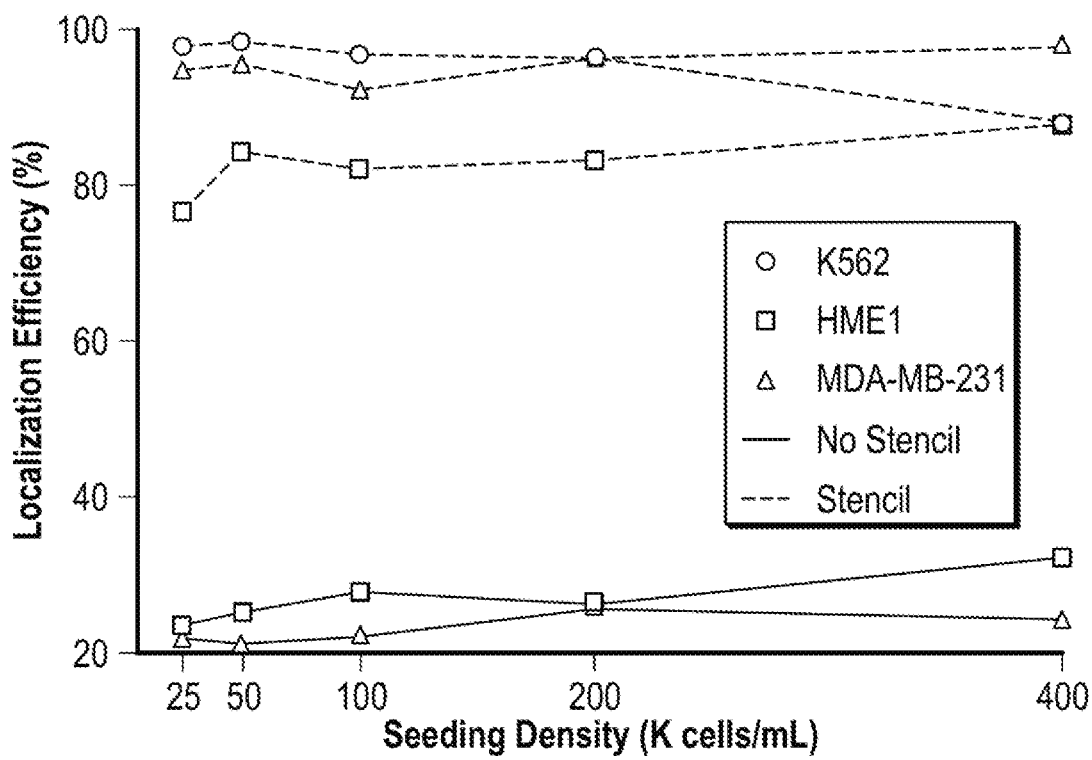
FIG. 13 provides plots of localization efficiency (percentage) as a function of seeding density (K cells/mL) for K562 cells seeded with a sacrificial film stencil, and for HME1 cells and MDA-MB-231 cells each seeded with and without a sacrificial film stencil.

Regarding the effects of seeding density, it was found that the enhanced localization efficiency provided by the seeding stencil was relatively independent of seeding density with a 4-fold average increase in localization efficiency across all seeding densities for MDA-MB-231 substrates and a 3-fold increase for HME1 substrates (t-test; $p<0.0001$) (as shown in FIG. 13). These findings confirm that the stencil is highly effective at controlling the localization of cells using various cell lines and across a wide range of seeding densities. The ability to efficiently pattern cells to defined locations is of significant value in single cell analysis.

Figure 14:
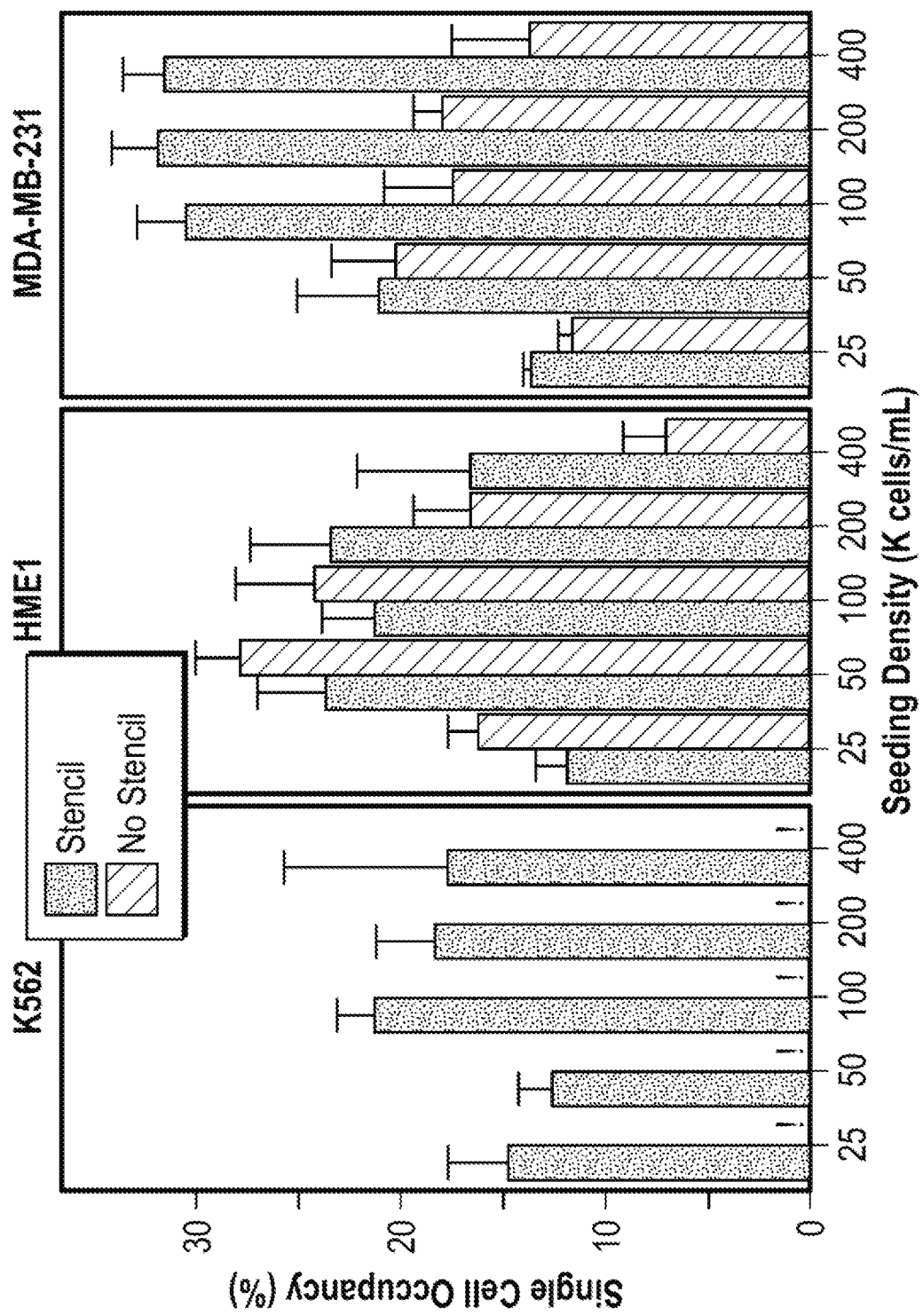
FIG. 14 is a bar chart of single cell occupancy percentage as a function of seeding density (K cells/mL) for K562 cells seeded with a sacrificial film stencil, and for HME1 cells and MDA-MB-231 cells each seeded with and without a sacrificial film stencil.

Thereafter, the frequency of single cell occupancy in microwells seeded through stencils disclosed herein was investigated. The relationship between the seeding density and the percentage of sampled microwells containing single cells (single cell occupancy) was found to exhibit different trends for each cell line. As shown in FIG. 14, the K562 cell line (which required the use of a stencil to achieve successful adhesion) exhibited very little correlation between seeding density and single cell occupancy, which remained at approximately 17% through all experimental densities. With continued reference to FIG. 14, single cell occupancies of HME1 cells trended toward a loosely parabolic dependence on seeding density, with densities near 50K cells/mL yielding the largest fraction of single-cell microwells for both stencil seeded and control cells. Stencil-seeded and directly-seeded HME1 cells did not differ significantly in single cell occupancy (Mann-Whitney U test: $p>0.1$). In contrast, single cell occupancies of MDA-MB-231 were positively impacted by stencil-seeding. As shown in FIG. 14, MDA-MB-231 stencil-seeded substrates with seeding densities above 50K cells/mL were found to be significantly higher (Mann-Whitney U test: $p<0.05$) than directly-seeded controls, averaging at about 31% single cell occupancy. It was observed that at high concentrations, these cells tend to clump together into loosely adherent aggregates.

Figure 15:
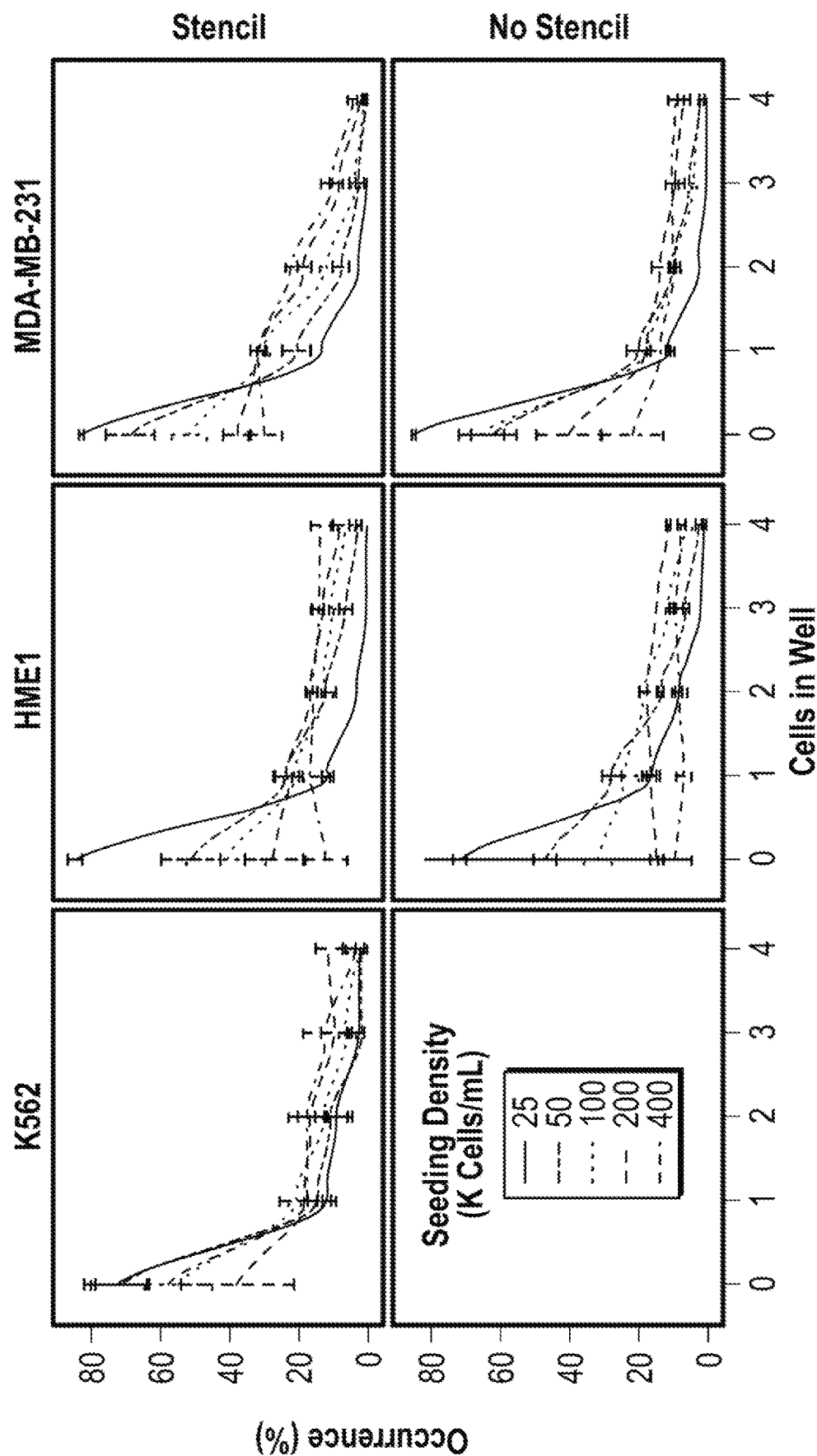
FIG. 15 provides microwell occupancy distributions plotting the percentage of microwells containing a specified number of cells at each of five seeding densities (25, 50, 100, 200, and 400 K cells/mL) for K562 cells seeded with a sacrificial film stencil, and for HME1 cells and MDA-MB-231 cells each seeded with and without a sacrificial film stencil.

It is therefore speculated that stencils as described herein function as a cellular sieve, favoring single cells or doublets, while inhibiting the passage of larger aggregates. The exhaustive distributions of empty, single, double, triple, and quadruple occupied microwells under various seeding conditions was also investigated, with results shown in FIG. 15. These data support the idea that the stencil shifts the balance of cell distribution in microwells toward single cells at the expense of microwells containing four cells in the MDA-MB-231 cell line. While considerably higher single cell occupancy, approaching 100%, can be achieved by modern microfluidic methods, the use of a stencil has the benefit of not subjecting the cells to the high shear stress environments or the impacts characteristic of high-throughput microfluidic devices. Further, the stencil design dramatically simplifies the cell loading procedure for the end user. Microfluidic-based cell patterning requires specialized equipment, expertise, and relatively demanding optimization. Use of patterning stencils described herein requires only standard cell culture skills and no specialized or costly equipment.

It has therefore been demonstrated that cell seeding stencils are highly effective at patterning cells into features of microfabricated substrates, and are readily adaptable to specific geometries and cell lines. Cell seeding methods described herein do not expose cells to any physical stresses beyond those of standard cell culture. Since cell seeding methods disclosed herein are based on a physical barrier instead of differential cell adhesion to achieve isolation, such methods do not select subpopulations of cells based on adhesion properties or expose cells to reactive substrates that may alter cellular physiology. Preparation of sacrificial film stencils as described herein is simple and low-cost, as evidenced by the fact that a stencil for a 2,980-microwell array can be prepared in less than an hour. For embodiments in which a sacrificial film stencil is fabricated while affixed to a cell seeding substrate, there is no need for microscale stencil-substrate alignment, dramatically simplifying its usage. Since the specificity of cell localization is based on the design of the sacrificial film stencil rather than the cell seeding technique, methods described herein are readily accessible to researchers in biological fields using standard cell culture techniques.

Embodiments disclosed herein provide one or more technical benefits over current technology, including, but not limited to: in situ hole patterning without the need for part alignment, restriction of cell seeding to specific regions of an underlying substrate (e.g., regions inside microwells), enhancing simplicity and speed of selective cell seeding, and reduction of potentially phenotypically discriminatory processes.

Upon reading the foregoing description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:
1. A method for seeding cells, the method comprising:
affixing a sacrificial film comprising a polymeric film to a cell seeding substrate defining a plurality of microwells, wherein each microwell of the plurality of microwells is elevated or recessed relative to a body structure connecting the plurality of microwells, and the affixing of the sacrificial film to the cell seeding substrate comprises selectively melting the polymeric film to a cover in multiple locations to locally adhere portions of the polymeric film to the cover in the multiple locations;

generating an array of holes in the sacrificial film by removing the cover, whereby upon removal of the cover, the locally adhered portions of the polymeric film remain adhered to the cover removed from the sacrificial film to generate the array of holes in the sacrificial film, wherein each hole of the array of holes is registered with a microwell of the plurality of microwells;

seeding cells through the array of holes onto the cell seeding substrate to yield a plurality of spatially localized cells; and removing the sacrificial film from the cell seeding substrate after the seeding of cells through the array of holes onto the cell seeding substrate;

wherein each hole of the array of holes has a width that is smaller than a maximum width of each microwell of the plurality of microwells.

2. The method of claim 1, further comprising incubating the plurality of spatially localized cells seeded onto the cell seeding substrate.

3. The method of claim 1, further comprising performing an assay utilizing the plurality of spatially localized cells, wherein the sacrificial film is removed prior to collection of data from the assay.

4. The method of claim 1, wherein;
the sacrificial film comprises a polymeric film,
the polymeric film comprises a main film structure; and
portions of the polymeric film are deposited into microwells of the plurality of microwells, and said portions are simultaneously separated from the main film structure, such that upon removal of the main film structure, film residue remains in the microwells or is otherwise vaporized or redistributed.

5. A method for seeding cells, the method comprising:
affixing a sacrificial film to a cell seeding substrate defining a plurality of microwells, wherein each microwell of the plurality of microwells is elevated or recessed relative to a body structure connecting the plurality of microwells, wherein the sacrificial film comprises a polymeric film, and the applying of the sacrificial film comprises selectively melting portions of the polymeric film onto a cover in multiple locations to locally compromise a structural integrity of the polymeric film and to locally adhere portions of the polymeric film to the cover in the multiple locations;

generating an array of holes in the sacrificial film by removing the cover, whereby upon removal of the cover, the locally adhered portions of the polymeric film remain adhered to the cover removed from the sacrificial film to generate the array of holes in the sacrificial film, wherein each hole of the array of holes is registered with a microwell of the plurality of microwells;

seeding cells through the array of holes onto the cell seeding substrate to yield a plurality of spatially localized cells; and removing the sacrificial film from the cell seeding substrate after the seeding of cells through the array of holes onto the cell seeding substrate.

6. The method of claim 5, further comprising incubating the plurality of spatially localized cells seeded onto the cell seeding substrate.

7. The method of claim 5, further comprising performing an assay utilizing the plurality of spatially localized cells.

8. The method of claim 7, wherein the removing the sacrificial film is performed prior to collection of data from the assay.

* * * * *